US012635860B2

(12) United States Patent
Chun et al.

(10) Patent No.: US 12,635,860 B2
(45) Date of Patent: May 26, 2026

(54) ANTI-BUCKLING DEVICES AND METHODS FOR SURGICAL SYSTEM

(71) Applicant: Noah Medical Corporation, San Carlos, CA (US)

(72) Inventors: Byron Liehwah Chun, San Francisco, CA (US); Hironori Baba, Emerald Hills, CA (US); Enrique Romo, Danville, CA (US); Anish Kumar Mampetta, Sunnyvale, CA (US)

(73) Assignee: Noah Medical Corporation, San Carlos, CA (US)

( * ) Notice: Subject to any disclaimer, the term of this patent is extended or adjusted under 35 U.S.C. 154(b) by 258 days.

(21) Appl. No.: 18/489,362

(22) Filed: Oct. 18, 2023

(65) Prior Publication Data

US 2024/0108203 A1     Apr. 4, 2024

Related U.S. Application Data

(63) Continuation of application No. PCT/US2022/025616, filed on Apr. 20, 2022.

(60) Provisional application No. 63/195,432, filed on Jun. 1, 2021, provisional application No. 63/181,105, filed on Apr. 28, 2021.

(51) Int. Cl.
*A61B 1/00* (2006.01)
*A61B 1/06* (2006.01)

(52) U.S. Cl.
CPC ...... *A61B 1/00154* (2013.01); *A61B 1/00137* (2013.01); *A61B 1/0014* (2013.01); *A61B 1/00149* (2013.01); *A61B 1/06* (2013.01)

(58) Field of Classification Search
CPC .............. A61B 1/00137; A61B 1/0014; A61B 1/00149; A61B 1/00154; A61B 1/06; A61B 1/005; A61B 2017/00991
USPC ........................................................ 600/132
See application file for complete search history.

(56) References Cited

U.S. PATENT DOCUMENTS

| | | | | |
|---|---|---|---|---|
| 5,876,326 A | * | 3/1999 | Takamura | .......... H01R 13/6581 |
| | | | | 600/110 |
| 6,689,050 B1 | * | 2/2004 | Beutter | .................. A61B 1/045 |
| | | | | 600/117 |
| 2001/0007917 A1 | * | 7/2001 | Hayakawa | ......... A61B 1/00071 |
| | | | | 600/920 |

(Continued)

FOREIGN PATENT DOCUMENTS

| | | |
|---|---|---|
| CN | 101553190 B | 6/2011 |
| CN | 209221293 U | 8/2019 |

(Continued)

OTHER PUBLICATIONS

PCT/US2022/025616 International Search Report and Written Opinion dated Sep. 21, 2022.

(Continued)

*Primary Examiner* — Aaron B Fairchild
(74) *Attorney, Agent, or Firm* — Wilson Sonsini Goodrich & Rosati

(57) ABSTRACT

An anti-buckling device is provided. The anti-buckling device comprises: a plurality of modular segments, and each modular segment comprises a cap and a tube. The cap comprises a support feature configured for supporting an elongate member and the tube comprises a coupling feature configured for engaging a given modular segment with another modular segment.

8 Claims, 29 Drawing Sheets

(56)          References Cited

U.S. PATENT DOCUMENTS

| | | |
|---|---|---|
| 2012/0071752 A1 | 3/2012 | Sewell et al. |
| 2018/0031018 A1 | 2/2018 | Muirhead |
| 2018/0070935 A1 | 3/2018 | Fenech |
| 2018/0126121 A1 | 5/2018 | Mauch |
| 2019/0247128 A1 | 8/2019 | Inouye et al. |
| 2019/0269885 A1 | 9/2019 | Bailey et al. |

FOREIGN PATENT DOCUMENTS

| | | |
|---|---|---|
| KR | 20020021909 A | 3/2002 |
| WO | WO-2021127426 A1 | 6/2021 |
| WO | WO-2022231923 A1 | 11/2022 |

OTHER PUBLICATIONS

Zhang et al.: The torsion transmission characteristics for gastroscope intervention. Proceedings of the 2018 IEEE International Conference on Intelligence and Safety for Robotics, Shenyang, China, Aug. 24-27, 2018; pp. 407-412.

* cited by examiner

211
HANDLE

221 IDM

213
CATHETER

QUICK RELEASE
TUBE FROM
BRACKET

ANTI-BUCKLING
TELESCOPING
TUBE
201

AB TUBE
SUPPORT
SURFACE
203

ET TUBE HOLDER
ATTACHMENT

ET TUBE MOUNT
SUPPORT
ARM

1003

1001

1201

1203

1200

1207

1205

1305

1303

1305

1301

1301

1501

1503

Inner Segment

Outer Segment

Inner Segment

Outer Segment

2005

2003

2000

2001

ANTI-BUCKLING DEVICES AND METHODS FOR SURGICAL SYSTEM

REFERENCE

This application is a continuation of International Application No. PCT/US2022/025616, filed Apr. 20, 2022, which claims priority to U.S. Provisional Patent Application No. 63/181,105, filed on Apr. 28, 2021, and U.S. Provisional Patent Application No. 63/195,432, filed on Jun. 1, 2021, each of which is entirely incorporated herein by reference.

BACKGROUND OF THE INVENTION

Endoscopy procedures use an endoscope to examine the interior of a hollow organ or cavity of the body. Unlike many other medical imaging techniques, endoscopes are inserted into the organ directly. Flexible endoscope that can deliver instinctive steering and control is useful in diagnosing and treating diseases that are accessible through any natural orifice in the body. Depending on the clinical indication, the endoscope may be designated as bronchoscope, ureteroscope, colonoscope, gastroscope, ENT scope, and various others.

SUMMARY OF THE INVENTION

Recognized herein is a need for a minimally invasive system that allows for performing surgical procedures or diagnostic operations with improved reliability and stability. The present disclosure provides robotic surgical systems and devices well suited for use in performing medical procedures. The surgical system may include a low-cost, single-use articulatable endoscope for diagnosis and treatment in various applications such as bronchoscopy, urology, gynecology, arthroscopy, orthopedics, ENT, gastro-intestine endoscopy, neurosurgery, and various others. The surgical system of the present disclosure may be a robotic endoscope system comprising an anti-buckling device. The anti-buckling device may improve the stability and accuracy for controlling the movement of an elongate member.

In some embodiments of the invention, the elongate member may be a catheter that is to be inserted into a body of a patient and can be disposable. For instance, the catheter portion may be designed to be disposable at low cost while preserving the surgical performance capability and functionality. It should be noted that the provided endoscope systems can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

In an aspect of the present disclosure, an anti-buckling device is provided. The anti-buckling device comprises: a plurality of modular segments, where each modular segment comprises a cap and a tube. The cap comprises a support feature configured for supporting an elongate member and the tube comprises a coupling feature configured for engaging a given modular segment with another modular segment.

In some embodiments, the elongate member comprises a proximal end and a distal end, where the proximal end is removably attached to a robotic arm via a handle, and the distal end is integrated with an imaging device, a position sensor and an illumination device. In some cases, the distal end comprises a structure to receive the imaging device, the position sensor, and the illumination device. In some cases, the imaging device, the position sensor, and the illumination device are arranged into a compact configuration. In some cases, the handle is connected to a first end of the anti-buckling device. In some cases, the handle comprises an interface configured to couple the handle to an instrument driving mechanism attached to the robotic arm. In some cases, the elongate member further comprises a bending section that is articulated by one or more pull wires.

In some embodiments, the support feature comprises a first opening having a dimension matches a dimension of the elongate member. In some embodiments, the support feature is configured to align a modular segment with a neighboring modular segment when they are in a collapse state.

In some embodiments, the cap is releasably coupled to the tube. In some embodiments, the anti-buckling device further comprises a locking feature for preventing the plurality of modular segments from moving when they are in a collapse state.

In another aspect, an anti-buckling device comprising a spiralized rolling structure is provided. The anti-buckling device comprises a spiralized rolling structure formed of a sheet of material for supporting an elongate member; a first component connected to a distal end of the spiralized rolling structure; and a second component is connected to a proximal end of the spiralized rolling structure. In some cases, the first component and the second component are releasably connected when the anti-buckling device is in a collapsed state.

In some embodiments, the material is paper or fabric. In some embodiments, the first component connects the anti-buckling device to a component at a patient bed. In some embodiments, the second component connects the anti-buckling device to a handle portion of the elongate member.

In some embodiments, the spiralized rolling structure provides a continuous support to the elongate member. In some embodiments, the first component connected to the distal end of the spiralized rolling structure via a third component. In some cases, the first component connected to the distal end of the spiralized rolling structure via the third component. In some instances, the third component provides support to a distal end of the elongate member. In some cases, the third component comprises a self-centering feature to assist in alignment when the anti-buckling device is in the collapsed state.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION OF THE INVENTION

Figure 1:
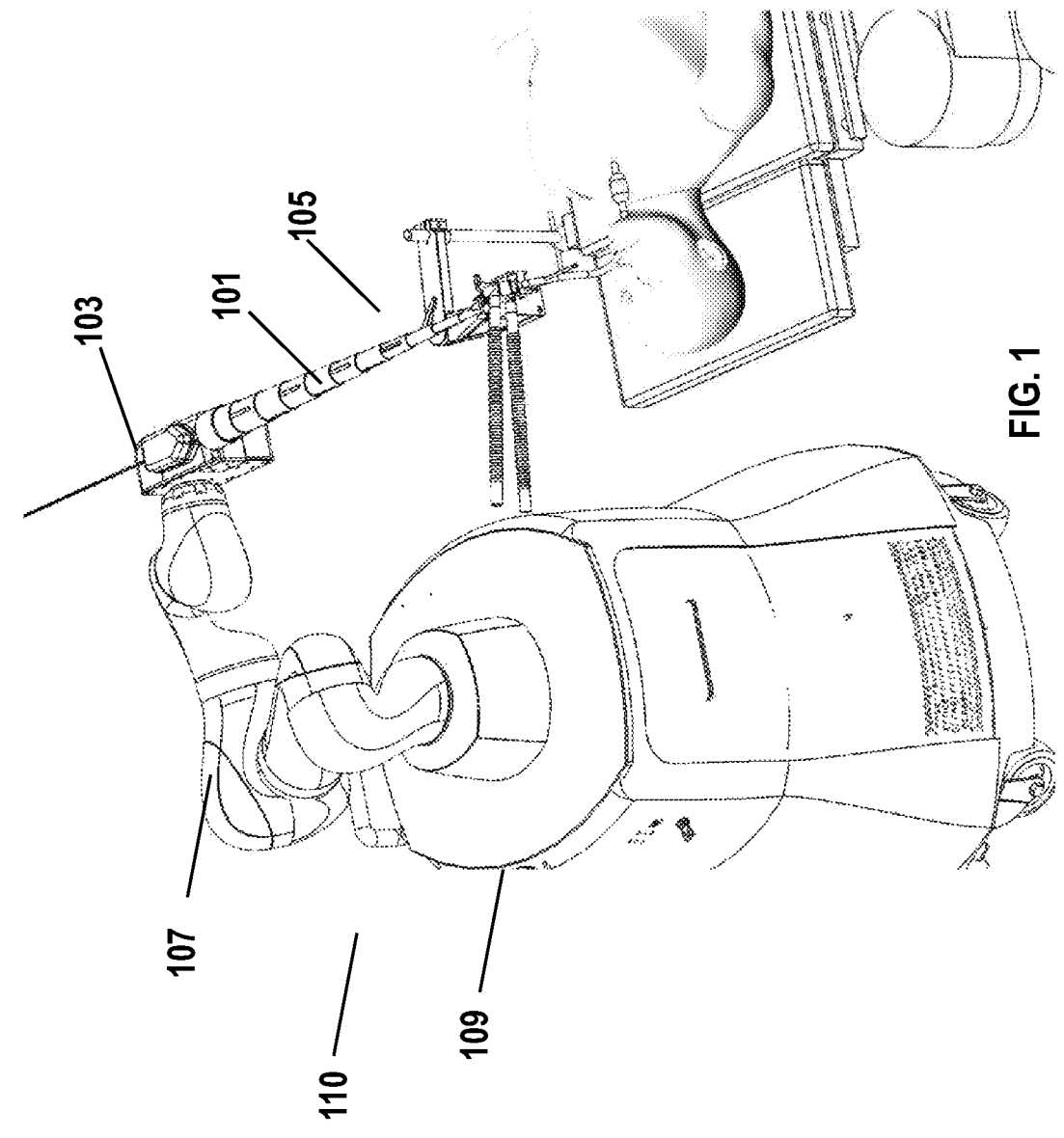
FIG. 1 shows an example of a robotic endoscope system, in accordance with some embodiments of the invention.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides anti-buckling devices and methods for a flexible elongate member in a surgical system. For example, when the flexible portions of catheter are inserted by extending mechanisms through bronchoscope into patients, one or more sections may bend or buckle. In some cases, to prevent the catheter from buckling while the endoscope is advanced towards the patient, an anti-buckling mechanism may be coupled to the robotic endoscope (e.g., the handle portion of the endoscope) to support the catheter.

While exemplary embodiments will be primarily directed at an articulable flexible endoscope, one of skill in the art will appreciate that this is not intended to be limiting, and the anti-buckling devices and methods described herein may be used for other flexible devices and can be utilized in various therapeutic or diagnostic procedures and in various anatomical regions of a patient's body such as a digestive system, including but not limited to the esophagus, liver, stomach, colon, urinary tract, or a respiratory system, including but not limited to the bronchus, the lung, and various others.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms distal and proximal may generally refer to locations referenced from the apparatus, and can be opposite of anatomical references. For example, a distal location of an endoscope or catheter may correspond to a proximal location of an elongate member of the patient, and a proximal location of the endoscope or catheter may correspond to a distal location of the elongate member of the patient.

A system as described herein, includes an elongate portion or elongate member such as a catheter. The terms "elongate member", and "catheter", are used interchangeably throughout the specification unless contexts suggest otherwise. The elongate member can be placed directly into the body lumen or a body cavity. In some embodiments, the system may further include a support apparatus such as a robotic manipulator (e.g., robotic arm) to drive, support, position or control the movements and/or operation of the elongate member. Alternatively or in addition to, the support apparatus may be a hand-held device or other control devices that may or may not include a robotic system. In some embodiments, the system may further include peripheral devices and subsystems such as imaging systems that would assist and/or facilitate the navigation of the elongate member to the target site in the body of a subject.

Existing anti-buckling mechanisms such as telescoping mechanisms may not have satisfactory performance such that the flexible portions of catheter may still bend or buckle. For instance, conventional anti-buckling devices may comprise a plurality of cylindrical tubes that are open end at both ends. The diameter of the cylindrical elements may increase gradually. These cylindrical tubes may be coupled together and can collapse or expand within each other. The diameter of the cylinder with smallest diameter is larger than the diameter of the elongate member therefore the elongate member can move forward when the cylinders are extended.

The diameter difference allows for the catheter to not be retrieved when the anti-buckling device is retracted or removed. However, the catheter may still buckle in the segments where the diameter of the telescoping mechanism is much greater than the outer diameter of the catheter. For example, as the diameter of the cylinders increases, the elongate member will not be brought into contact with the wall of the relatively larger tubes until a greater bending occurs.

The present disclosure provides an improved anti-buckling mechanism. The anti-buckling mechanism is used for preventing buckling of an insertion shaft or catheter with improved anti-buckling performance. The anti-buckling mechanism may comprise a plurality of modular segments that extend and collapse to support catheter delivery as it is inserted and retracted into and from a body of a patient. In some embodiments, each of the modular segment of the anti-buckling mechanism may comprise an internal structure to achieve anti-buckling of a catheter during the insertion and withdrawal with improved stability. The plurality of modular segments may be designed to allow for easy assembly and disassembly. For example, a modular segment can be easily swapped out. In some cases, multiple modular segments may be coupled/decoupled without extra coupling means (e.g., adhesives, screws, etc.).

In some embodiments, the plurality of modular segments may unintentionally extend, making it difficult to insert catheter during operation. They may also fall out due to gravity for force. The provided anti-buckling mechanism may include locking feature to prevent unwanted extension.

In some embodiments of the present disclosure, a robotic endoscope system is provided for performing surgical operations or diagnosis with improved performance at low cost. For example, the robotic endoscope system may comprise a steerable catheter that can be entirely disposable. FIG. 1 shows an example of a robotic endoscope system, in accordance with some embodiments of the invention. As shown in FIG. 1, the robotic endoscope system may comprise a steerable catheter assembly 105 and a robotic support system 110, for supporting or carrying the steerable catheter assembly. The steerable catheter assembly can be an endoscope. In some embodiments, the steerable catheter assembly may be a single-use robotic endoscope. In some embodiments, the robotic endoscope system may comprise an instrument driving mechanism 103 that is attached to the arm of the robotic support system. The instrument driving mechanism may be provided by any suitable controller device (e.g., hand-held controller) that may or may not include a robotic system. The instrument driving mechanism may provide mechanical and electrical interface to the steerable catheter assembly 105. The mechanical interface may allow the steerable catheter assembly 105 to be releasably coupled to the instrument driving mechanism 103. For instance, a handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool. The instrument driving mechanism may be used to control the elongate member or robotic catheter assembly in two or more degrees of freedom (e.g., articulation).

The robotic support system may comprise a robotic arm 107 and a mobile cart 109. The robotic arm 107 may initiate the positioning of the robotic catheter assembly or other robotic instrument. In some cases, a user interface, robotic control modules, and the robotic arm may be mounted to the mobile cart. The mobile cart may include various elements such as rechargeable power supply in electrical communication with an electric panel providing charging ports for portable electronic devices, converters, transformers and surge protectors for a plurality of AC and DC receptacles as power source for the on-board equipment including one or more computers storing application specific software for the user interface. The robotic arm, robotic endoscope system, user interface, catheter assembly and other components of the system can be the same as those described in International Application No. PCT/US20/65999, filed on Dec. 18, 2020, the disclosure of which is incorporated herein by reference in its entirety.

The steerable catheter assembly 105 may comprise a flexible elongate member that is coupled to a handle portion. The robotic endoscope system may comprise an anti-buckling device 101 for preventing the buckling of the elongate member during use. The anti-buckling devices will be described in further detail below.

Figure 2:
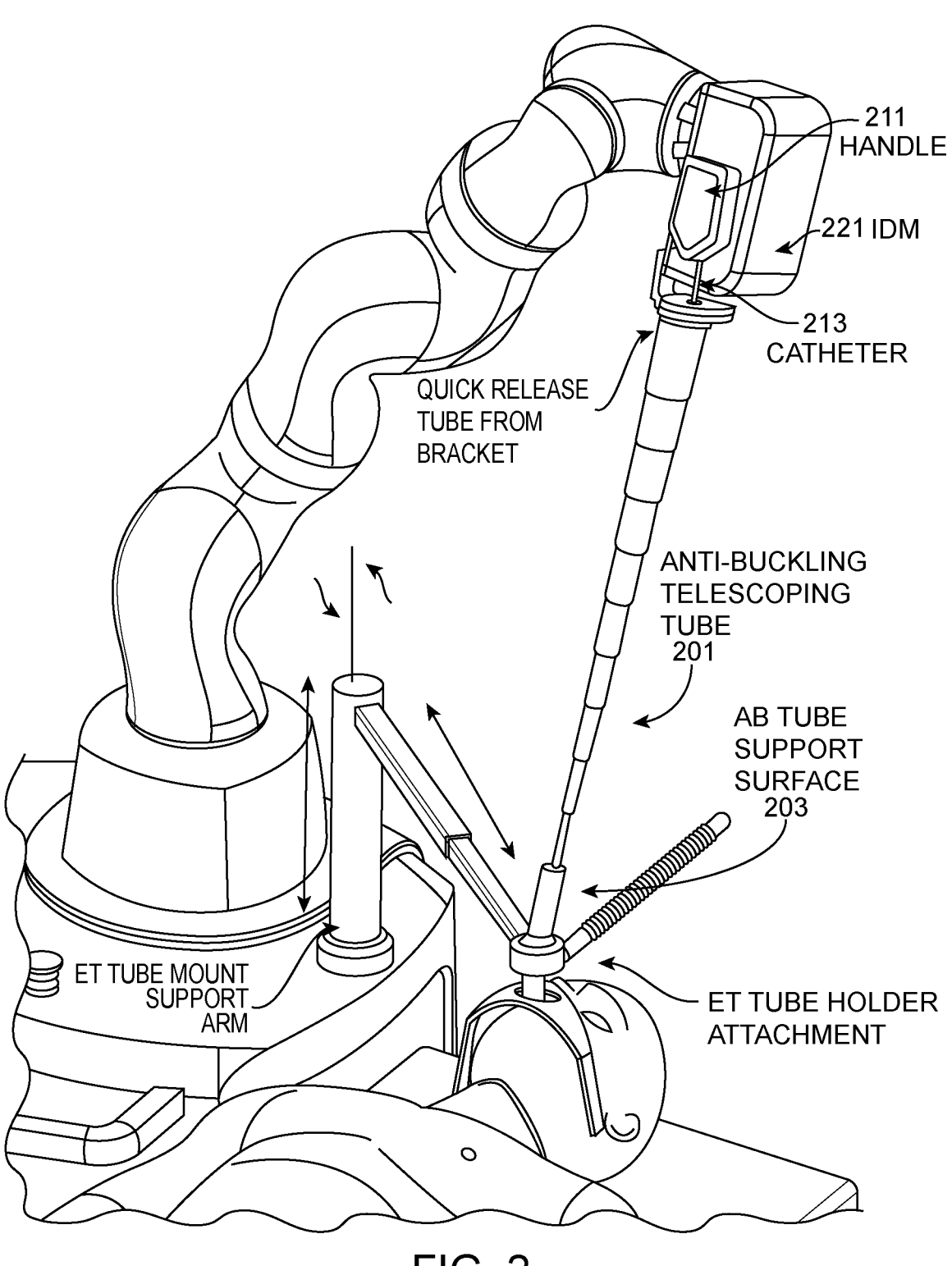
FIG. 2 shows an example of a robotic catheter assembly with an anti-buckling device.

FIG. 2 shows another example of a robotic catheter assembly with an anti-buckling device 201. The steerable catheter assembly may comprise a handle portion 211 that may include components configured to process image data, provide power, or establish communication with other external devices. For instance, the handle portion 211 may include a circuitry and communication elements that enables electrical communication between the steerable catheter assembly and the instrument driving mechanism 221, and any other external system or devices. In another example, the handle portion 211 may comprise circuitry elements such as power sources for powering the electronics (e.g., camera and LED lights) of the endoscope. In some cases, the handle portion may be in electrical communication with the instrument driving mechanism 221 via an electrical interface (e.g., printed circuit board) so that image/video data and/or sensor data can be received by the communication module of the instrument driving mechanism and may be transmitted to other external devices/systems. Alternatively or in addition to, the instrument driving mechanism 221 may provide a mechanical interface only. The handle portion may be in electrical communication with a modular wireless communication device or any other user device (e.g., portable/hand-held device or controller) for transmitting sensor data and/or receiving control signals.

The steerable catheter assembly may comprise a flexible elongate member 213 (i.e., catheter) that is coupled to the handle portion 211. In some embodiments, the flexible elongate member may comprise a shaft, steerable tip and a steerable section. The steerable catheter assembly may be a single use robotic endoscope. In some cases, only the elongate member may be disposable. In some cases, at least a portion of the elongate member (e.g., shaft, steerable tip, etc) may be disposable. In some cases, the entire steerable catheter assembly including the handle portion and the elongate member can be disposable. The flexible elongate member and the handle portion are designed such that the entire steerable catheter assembly can be disposed of at low cost.

The robotic endoscope can be releasably coupled to an instrument driving mechanism 221. The instrument driving mechanism 221 may be mounted to the arm of the robotic support system or to any actuated support system as described above. The instrument driving mechanism may provide mechanical and electrical interface to the robotic endoscope. The mechanical interface may allow the robotic endoscope to be releasably coupled to the instrument driving mechanism. For instance, the handle portion of the robotic endoscope can be attached to the instrument driving mechanism via quick install/release means, such as magnets and spring-loaded levels. In some cases, the robotic endoscope may be coupled or released from the instrument driving mechanism manually without using a tool. In some embodiments, the instrument driving mechanism 221 may comprise a set of motors that are actuated to rotationally drive a set of pull wires of the catheter. The handle portion 211 of the catheter assembly may be mounted onto the instrument drive mechanism so that its pulley assemblies are driven by the set of motors. The number of pulleys may vary based on the pull wire configurations. In some cases, one, two, three, four, or more pull wires may be utilized for articulating the catheter.

The handle portion may be designed allowing the robotic endoscope to be disposable at reduced cost. For instance, classic manual and robotic endoscope may have a cable in the proximal end of the endoscope handle. The cable often includes illumination fibers, camera video cable, and other sensors fibers or cables such as EM sensors, or shape sensing fibers. Such complex cable can be expensive adding to the cost of the endoscope. The provided robotic endoscope may have an optimized design such that simplified structures and components can be employed while preserving the mechanical and electrical functionalities. In some cases, the handle portion of the robotic endoscope may employ a cable-free design while providing a mechanical/electrical interface to the catheter.

In some case, the handle portion may be housing or comprise components configured to process image data, provide power, or establish communication with other external devices. In some cases, the communication may be wireless communication. For example, the wireless communications may include Wi-Fi, radio communications, Bluetooth, IR communications, or other types of direct communications. Such wireless communication capability may allow the robotic bronchoscope function in a plug-and-play fashion and can be conveniently disposed after single use. In some cases, the handle portion may comprise circuitry elements such as power sources for powering the electronics (e.g. camera and LED light source) disposed within the robotic bronchoscope or catheter.

The handle portion may be designed in conjunction with the catheter such that cables or fibers can be eliminated. For instance, the catheter portion may employ a design having a single working channel allowing instruments to pass through the robotic bronchoscope, as well as low cost electronics such as a chip-on-tip camera, illumination sources such as light emitting diode (LED) and EM sensors located at optimal locations in accordance with the mechanical structure of the catheter. This may allow for a simplified design of the handle portion. For instance, by using LEDs for illumination, the termination at the handle portion can be based on electrical soldering or wire crimping alone. For example, the handle portion may include a proximal board where the camera cable, LED cable, and EM sensor cable terminate to while the proximal board connects to the interface of the handle portion and establishes the electrical connections to the instrument driving mechanism. As described above, the instrument driving mechanism is attached to the robot arm (robotic support system) and provide a mechanical and electrical interface to the handle portion. This may advantageously improve the assembly and implementation efficiency as well as simplify the manufacturing process and cost. In some cases, the handle portion along with the catheter may be disposed of after a single use.

In some embodiments, the steerable catheter assembly may have a substantially integral design that one or more components may be integral to the catheter thereby simplifying the assembly, manufacturing process while preserving the kinematic, dynamic performance of the steerable catheter. As shown in the example, the steerable catheter assembly may comprise an elongate member 213 or a probing portion that is brought into proximity to the tissue and/or area that is to be examined. The elongate member 213 may, in some cases, also be referred to as catheter. The catheter 213 may comprise internal structures such as a working channel allowing tools to be inserted through. As an example, the working channel may have a dimension such as diameter of around 2 mm to be compatible with standard tools. The working channel may have any other suitable dimensions based on the application.

The catheter 213 may be composed of suitable materials for desired flexibility or bending stiffness. In some cases, the materials of the catheter may be selected such that it may maintain structural support to the internal structures (e.g., working channel) as well as being substantially flexible (e.g., able to bend in various directions and orientations). For example, the catheter can be made of any suitable material such as urethane, vinyl (such as polyvinyl chloride), Nylon (such as vestamid, grillamid), pellethane, polyethylene, polypropylene, polycarbonate, polyester, silicon elastomer, acetate and so forth. In some cases, the materials may be polymer material, bio-compatible polymer material and the catheter may be sufficiently flexible to be advancing through a path with a small curvature without causing pain to a subject. In some cases, the catheter may comprise a sheath. The sheath may not be the same length of the catheter. The sheath may be shorter than the catheter to provide desired support. Alternatively, the catheter may be substantially a single-piece component.

In some case, the distal portion or tip of the catheter may be substantially flexible such that it can be steered into one or more directions (e.g., pitch, yaw). In some embodiments, the catheter may have variable bending stiffness along the longitudinal axis direction. For instance, the catheter may comprise multiple segments having different bending stiffness (e.g., flexible, semi-rigid, and rigid). The bending stiffness may be varied by selecting materials with different stiffness/rigidity, varying structures in different segments, adding additional supporting components or any combination of the above. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires. The distal portion of the catheter may be made of any suitable material such as co-polymers, polymers, metals or alloys such it can be bent by the pull wires. In some embodiments, the proximal end or portion of one or more pull wires may be operatively coupled to various mechanisms (e.g., gears, pulleys, etc.) in the handle portion of the catheter assembly. The pull wire may be a metallic wire, cable or thread, or it may be a polymeric wire, cable or thread. The pull wire can also be made of natural or organic materials or fibers. The pull wire can be any type of suitable wire, cable or thread capable of supporting various kinds of loads without deformation, significant deformation, or breakage. The distal end or portion of one or more pull wires may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

As described above, the pull wires may be made of any suitable material such as stainless steel (e.g. SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals.

The catheter may have a dimension so that one or more electronic components can be integrated to the catheter. For example, the outer diameter of the distal tip may be around 4 to 4.4 millimeters (mm), and the diameter of the working channel may be around 2 mm such that one or more electronic components can be embedded into the wall of the catheter or the interstitials of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

In some embodiments, the catheter may be designed to be flexible. When the flexible portions of catheter are inserted by extending mechanisms through endoscope into patients, one or more sections may bend or buckle. The present disclosure provides an anti-buckling mechanism 201 may be coupled to the handle portion of the robotic endoscope to support the catheter.

The present disclosure provides an improved anti-buckling mechanism. The anti-buckling mechanism is used for preventing buckling of the insertion shaft. The anti-buckling mechanism 201 may be a telescopic extending device with internal mechanism to achieve anti-buckling of catheter during the insertion and withdrawal. The anti-buckling mechanism 201 may be detachably connected to the handle portion of the robotic endoscope at one end, and may be detachably connected to a support surface 203 at the other end. The anti-buckling mechanism may include a distal plate at the distal end that is attached to a fixture that is fastened to the patient's bed through a tube holder attachment. The fixture can be a post fastened to the bed in which case no extra force may be imposed to the patient when the anti-buckling device collapses. In the other embodiments, the fixture can be a railing on the bed.

Figure 3:
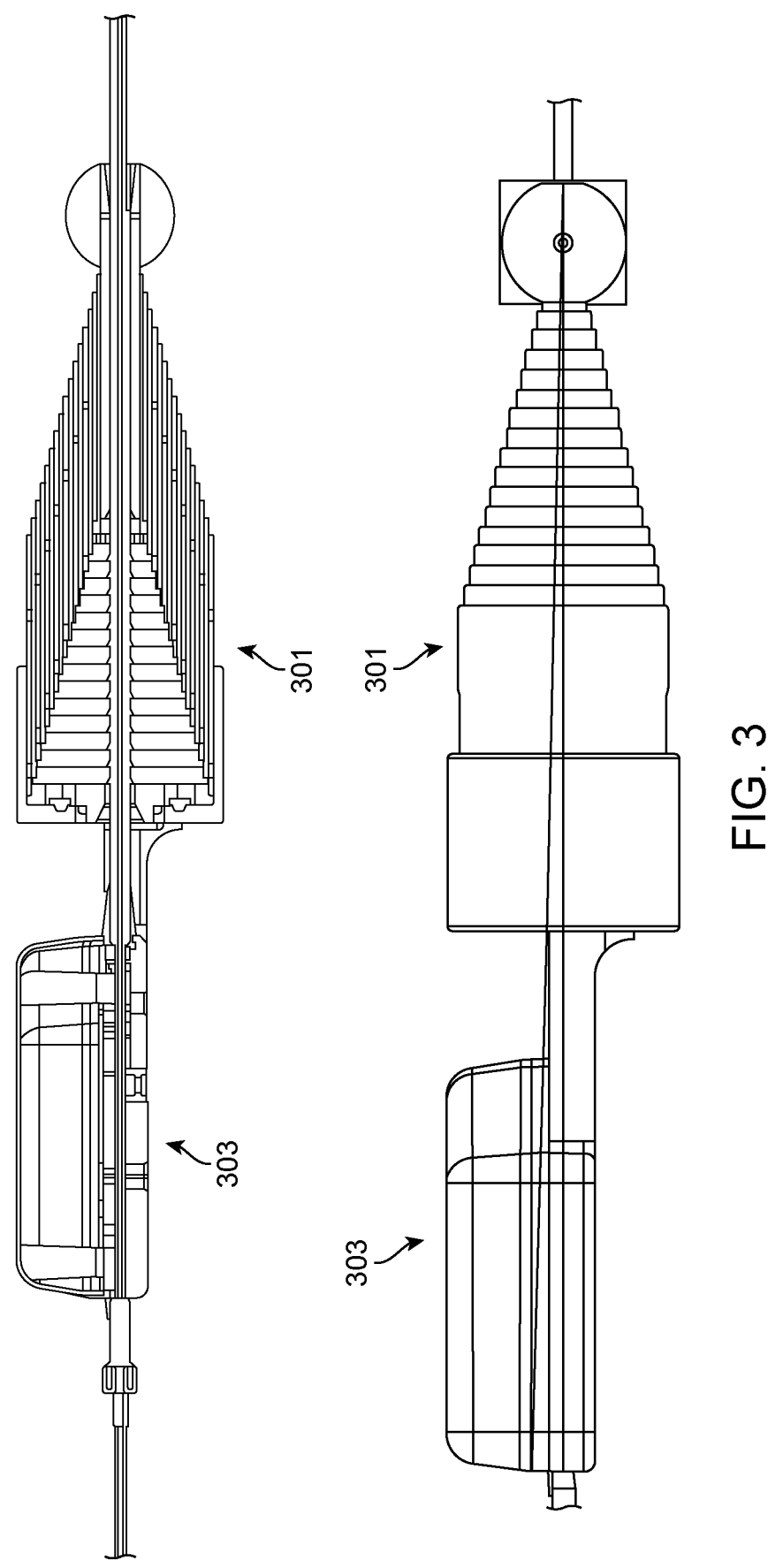
FIG. 3 shows examples of an assembly of an anti-buckling mechanism and a handle.

As shown in the example, the anti-buckling tube may be attached to a bracket on the instrument driving mechanism and may be removable and disposable after the procedure via quick release mechanism. A support arm may be supported by the robotic mobile cart that supports the endotracheal tube mount and provides a support surface for the distal end of the anti-buckling tube to press against as it is compressed. The support arm may be controlled to rotate, translate vertically up and down and/or may a boom arm that expands and contracts, such that it can be precisely positioned over the patients mouth and attached to the endotracheal tube mount. The support arm positioning may be synchronized with the movement of the robotic arm that it may track the location of the point of entry of the catheter. FIG. 3 shows examples of an assembly of the anti-buckling mechanism 301 and a handle 303. The examples show an anti-buckling mechanism that is connected to a handle and in a retracted/collapsed state and in a fully extended state.

Figure 4:
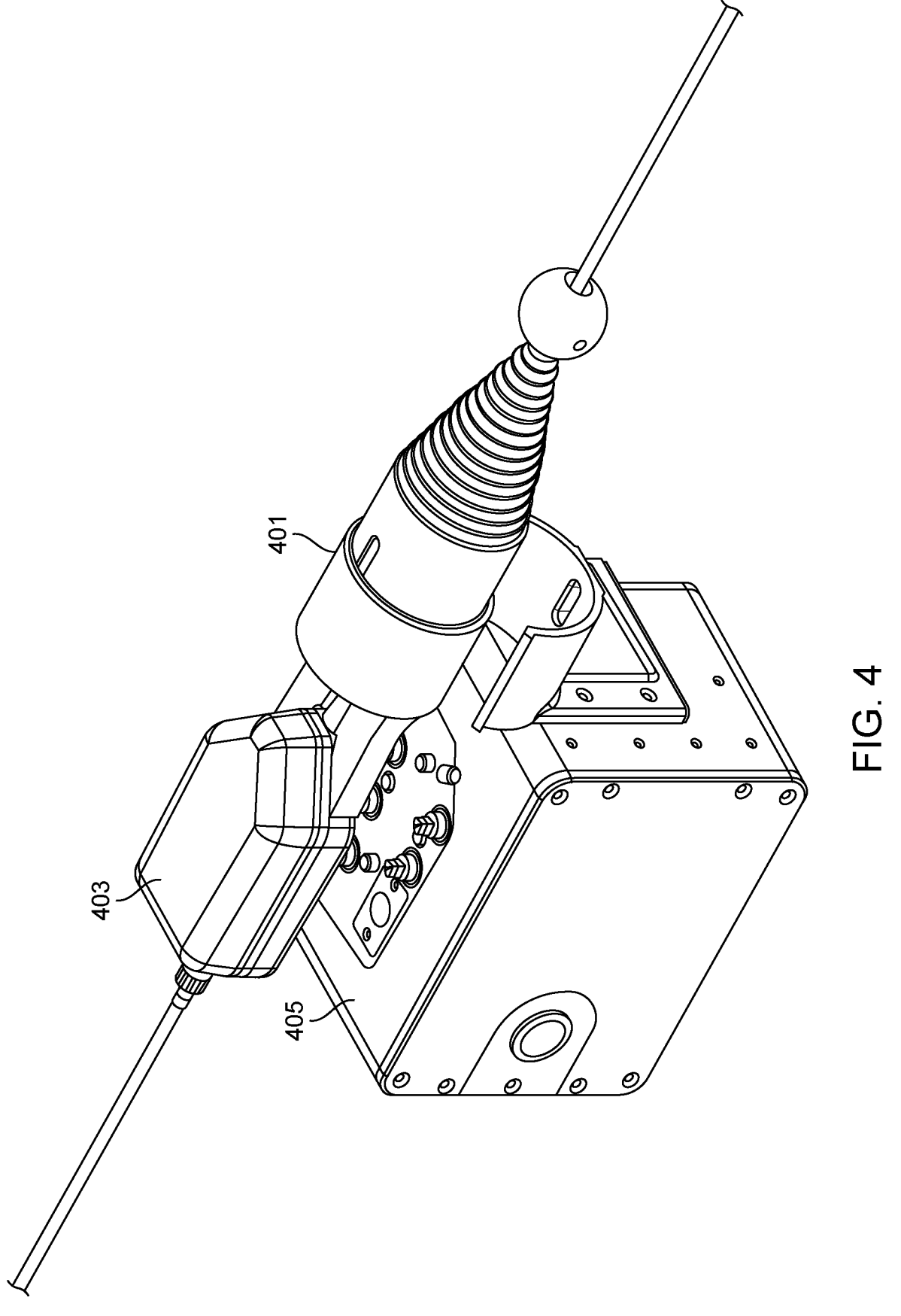
FIG. 4 shows an example of scope handle and anti-buckling tube assembly.
Figure 5:
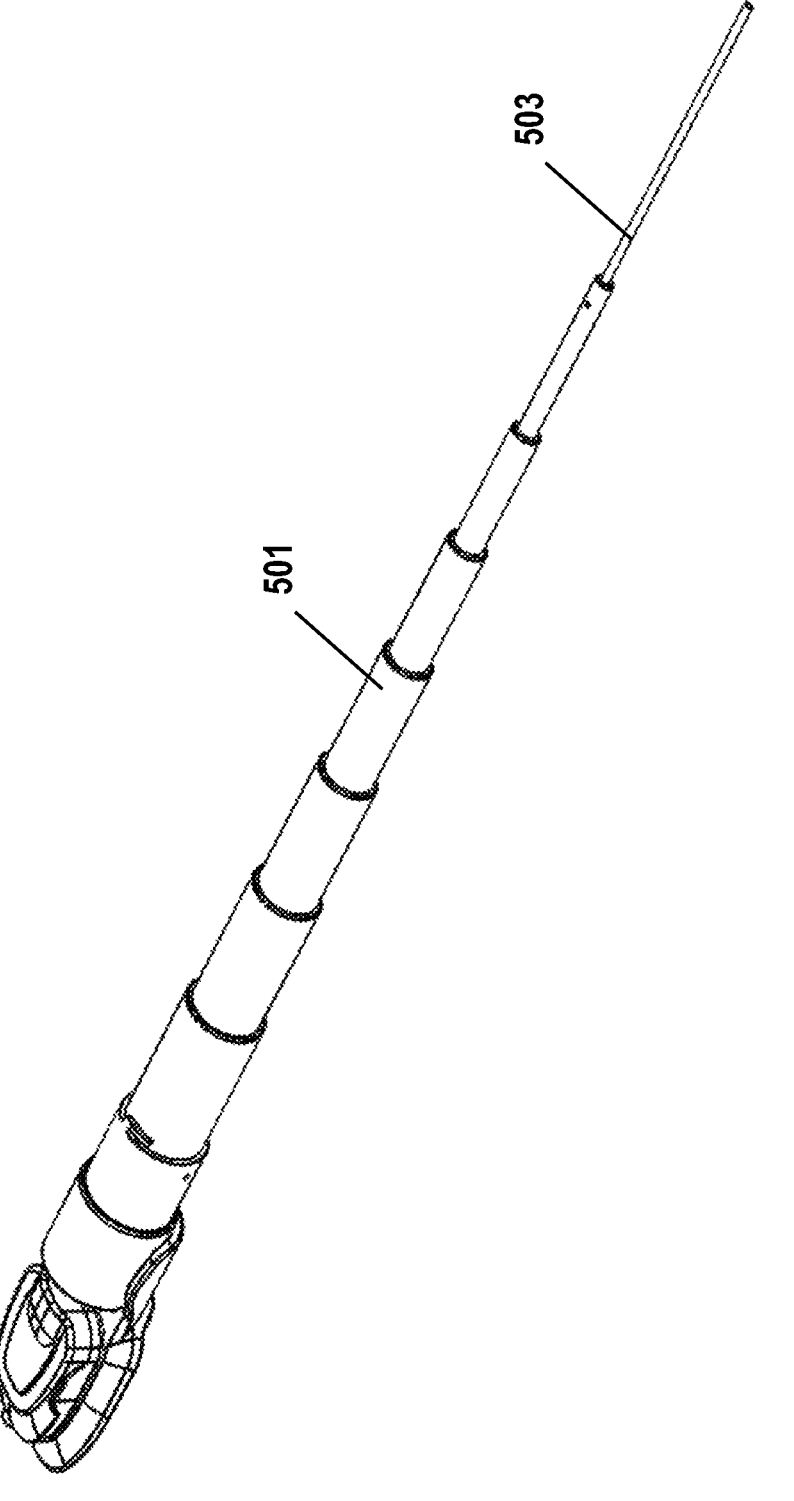
FIG. 5 and FIG. 6 show examples of an assembly of an anti-buckling device and a catheter assembly.
Figure 6:
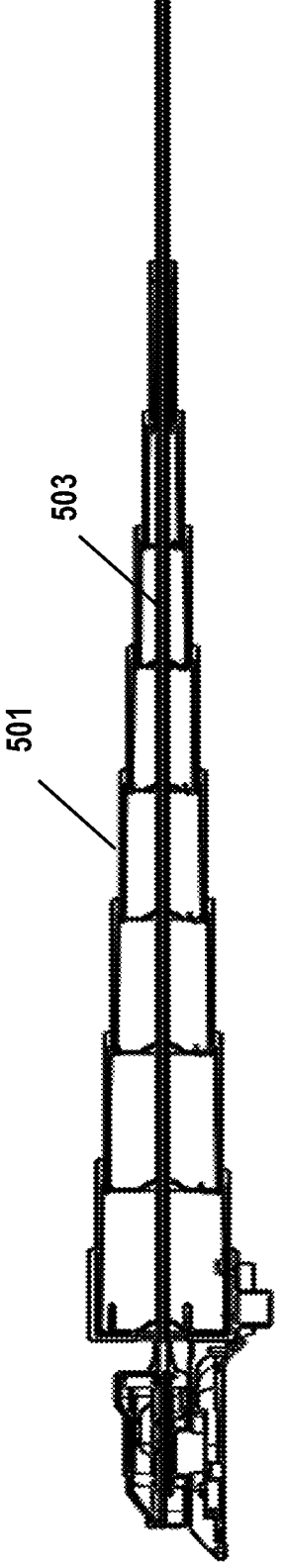

In some cases, the system and devices herein may allow for a simplified set-up flow for assembling the anti-buckling mechanism and the endoscope. For example, the anti-buckling mechanism and scope handle may be assembled via a lateral connection between the anti-buckling mechanism and the scope handle and top-load the assembled pieces as a single piece onto the instrument driving mechanism. This convenient assembly capability beneficially allows coupling the scope handle and anti-buckling assembly to the robotic arm regardless the state and current position of the instrument driving mechanism. FIG. 4 shows an example of scope handle and anti-buckling tube assembly. The anti-buckling device can be releasably connected to the handle via a connection feature. This allows a user to place the connected assembly of the anti-buckling device 401 and the scope onto the instrument driving mechanism 405 via the interface of the handle 403. Assembling the scope, and anti-buckling mechanism prior to loading it onto the instrument driving mechanism may beneficially simplify the workflow. FIG. 5 and FIG. 6 show examples of the assembly of the anti-buckling device 501 and the scope (catheter assembly) 503. In some cases, the anti-buckling device may be a separable device that can be disposed of after single use. Alternatively, the anti-buckling device may be reused or suitable for multiple uses.

Figure 7:
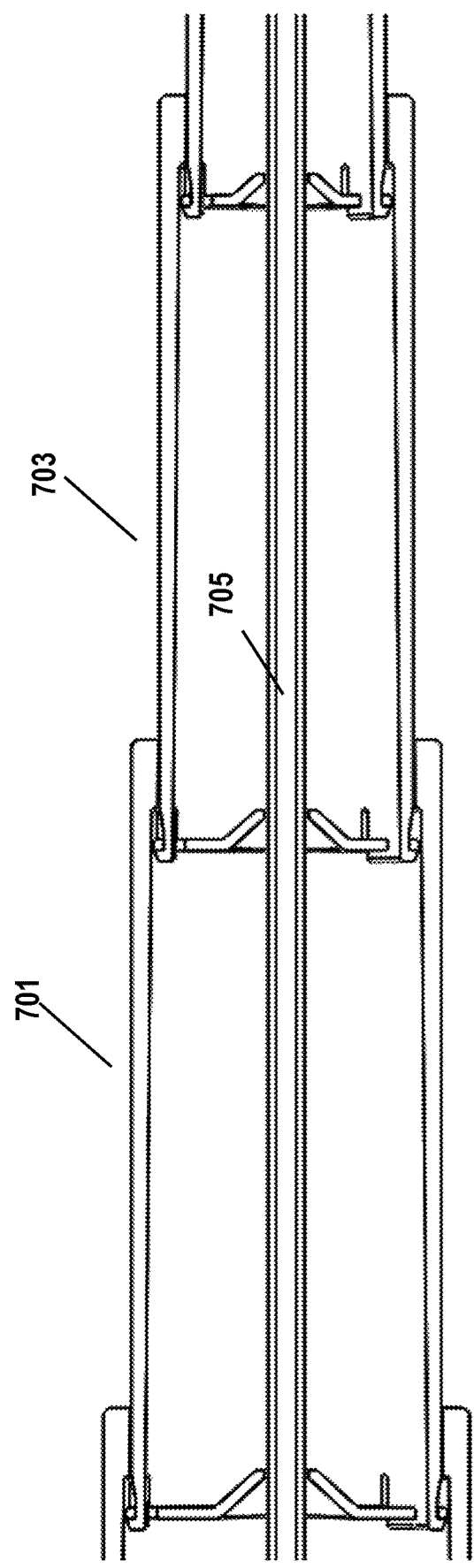
FIG. 7 shows an example of a plurality of telescoping segments of an anti-buckling mechanism, in accordance with some embodiments of the invention.

The anti-buckling mechanism may comprise a plurality of telescoping segments connected sequentially. FIG. 7 shows an example of a plurality of telescoping segments of the anti-buckling mechanism, in accordance with some embodiments of the invention.

In some embodiments, the anti-buckling device may include a plurality of modular segments 701, 703 with gradual reduction in the dimensions (e.g., diameter of the modular segment). The modular segments may also be referred to as telescoping segments which are used interchangeably throughout the specification. The plurality of modular segments may be concentrically assembled or connected along the axial axis.

In some embodiments, each modular segment may comprise a cap and a tube. The cap may include internal features such as a support feature to prevent the catheter 705 from buckling. During use, the catheter or elongate member 705 may be placed within the anti-buckling device. As the handle portion or instrument driving device is advanced distally, the plurality of modular segments may retract relative to each other to form a shorten configuration. As the handle portion or instrument driving device is moved proximally, the plurality of modular segments extend out of their respective neighboring tubes to form a lengthen configuration.

The catheter (elongate member) is housed within the lumen formed collectively by the tubes and is prevented from buckling by the supporting features of the caps. The elongate member may be supported by the supporting features of the cap of each modular segment. A small bending of the elongate member will bring the elongate member into contact with the cap (e.g., supporting feature of the cap) of the respective modular segment such that any buckling throughout the entire length of the elongate member is effectively prevented. This advantageously prevents the elongate member from buckling in any direction and in any location along the length inside the anti-buckling device regardless of the outer dimension of the plurality of modular segment.

In some embodiments, the tube may be formed with coupling features to enable convenient coupling with another tube without requiring additional coupling means (e.g., glue, fasteners, etc.). This may beneficially allow for easy swapping out a modular segment or replacing it with a new/different segment. The quick coupling and release feature may also allow for an adjustable anti-buckling device by adding/removing one or more modular segments from the distal end and/or the proximal end.

Figure 8:
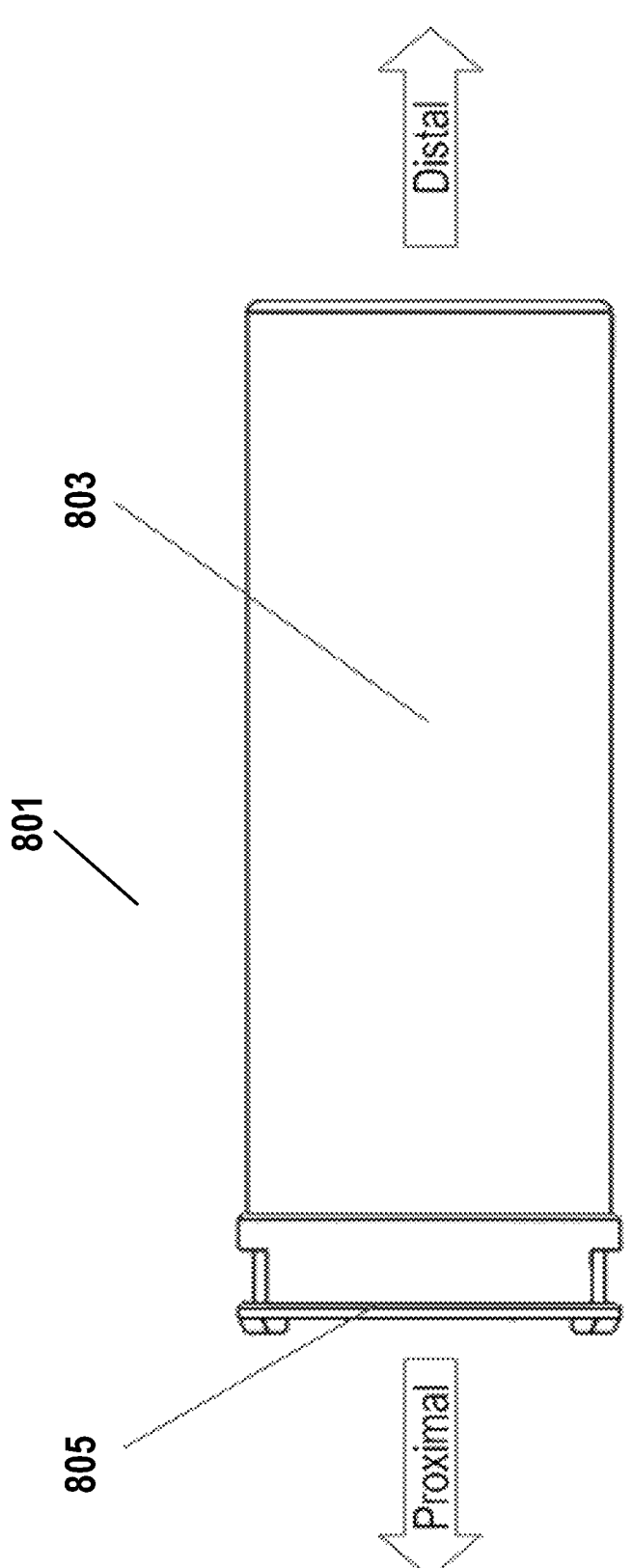
FIG. 8 and FIG. 9 show an example of a modular segment.
Figure 9:
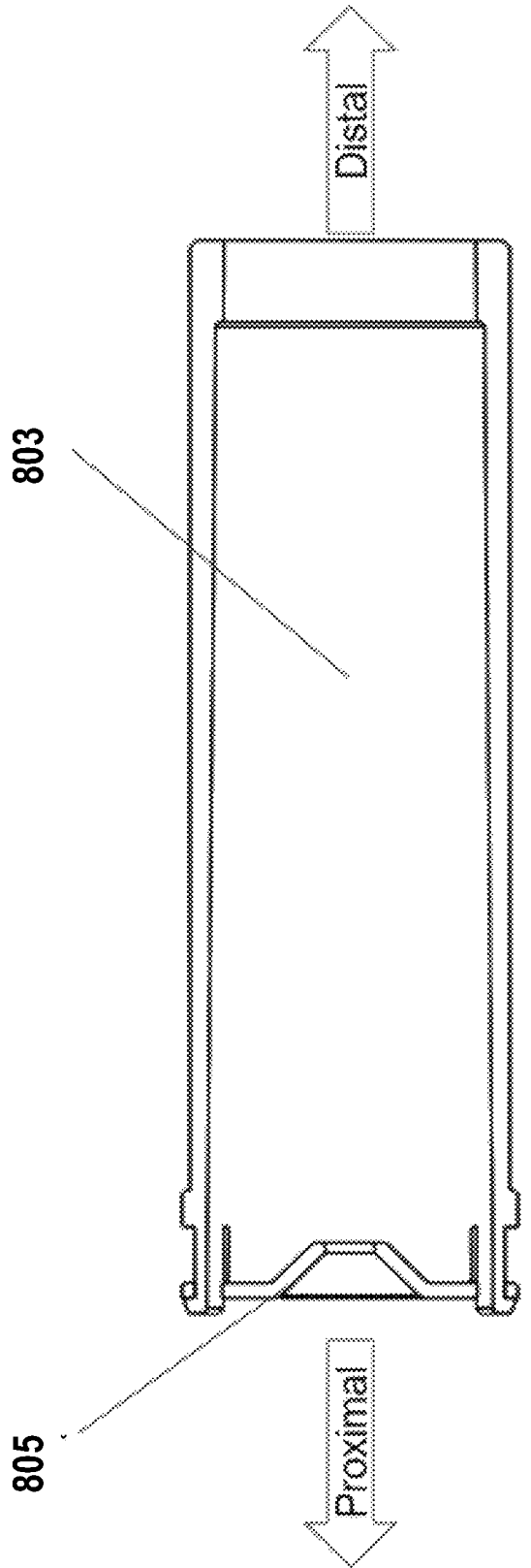

FIG. 8 and FIG. 9 show an example of a modular segment 801. FIG. 9 shows a cross-section view of the modular segment. A modular segment 801 may comprise a tube component 803 and a cap component 805. The tube component and cap component may be releasably coupled together to form the modular segment such as via a coupling feature. The coupling feature may be integrally formed on the tube component and/or the cap component such that additional coupling means may not be required. In some cases, the coupling feature may include a snap feature. The cap may be connected to the tube without requiring additional tools or coupling means. For example, the cap may be snapped onto the tube at one end of the tube. In some cases, the cap may be assembled to the tube at a proximal end. Alternatively, the cap may be assembled to the tube at a distal end.

Figure 10:
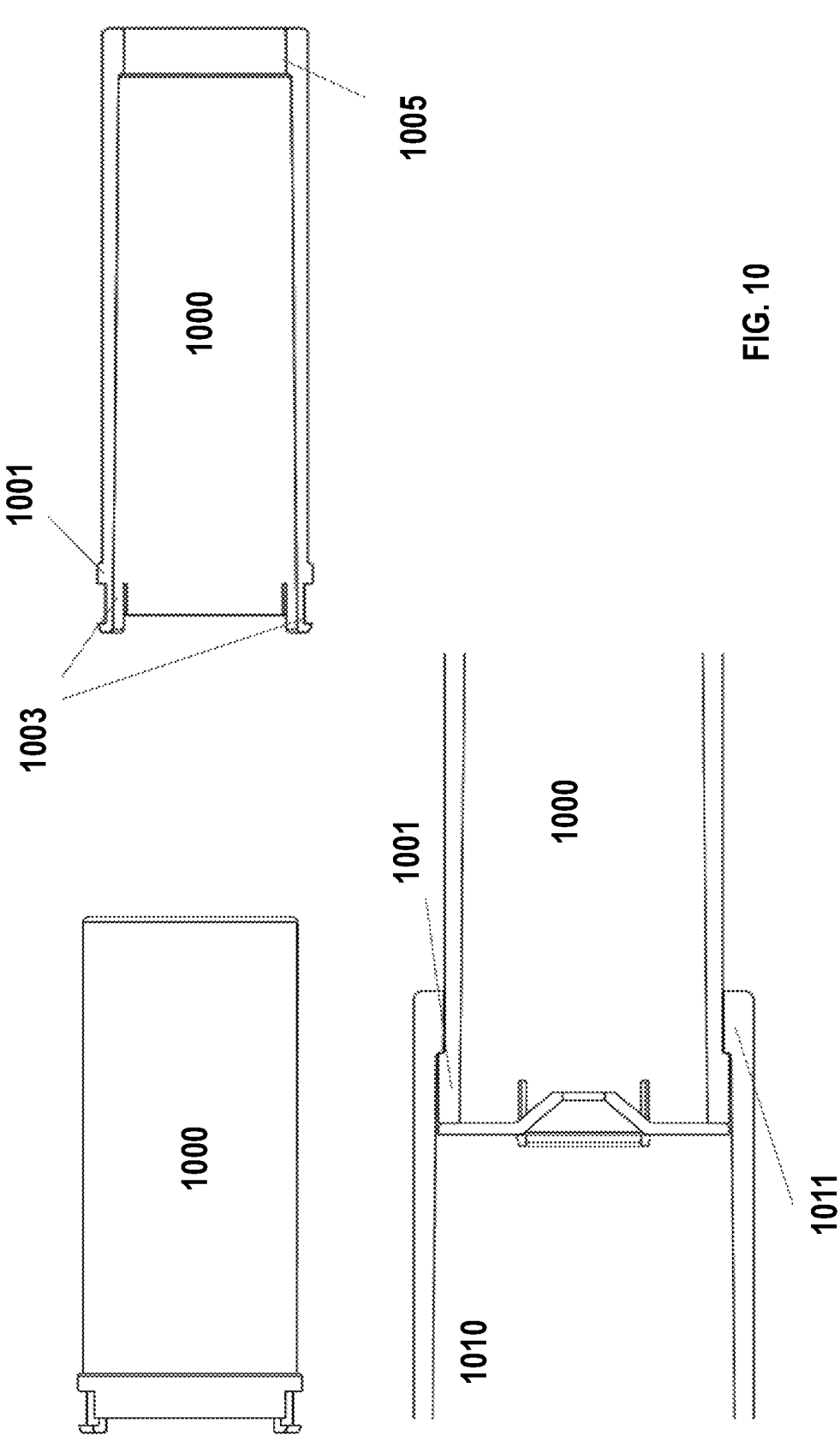
FIG. 10 shows an example of a tube component.

An assembled modular segment may be releasably coupled to another modular segment via a coupling structure. FIG. 10 shows an example of a tube component 1000. A tube component may have a cross-section in any suitable shape (e.g., circular, rectangular, etc.). In the illustrated example, the tube component 1000 may be substantially a cylinder that consist of a thin wall. In some cases, the interior surface of the tube may have a draft angle for injection molding. This draft angle also helps prevent the modular segments from drooping as they are extended. Alternatively, the interior surface of the tube may not have a draft angle. The tube can be manufactured using any suitable manufacturing methods such as injection molding, CNC machining, blow molding, 3D printing and various other methods.

The tube may comprise a coupling structure to engage the tube with a tube of another modular segment. In some cases, the coupling structure may include an inner stopping lip feature 1005 at a first end, and an outer stopping lip feature 1001 at the opposing end of the tube. The outer stopping lip feature (e.g., a radial protrusion slightly larger than the outer diameter of the cylinder) may prevent the respective modular segment from disengaging from the neighboring outer modular segment. The inner stopping lip feature may prevent a neighboring inner modular segment from disengaging from the respective modular segment. In some cases, the inner stopping lip feature 1005 and the outer stopping lip feature 1001 may be integrally formed with the tube.

The inner stopping lip feature and the outer stopping lip feature may prevent the detachment of the tubes/modular segments during extending the anti-buckling device. For example, a tube of the neighboring outer modular segment 1010 may engage with the tube of the modular segment 1000 via the inner stopping lip feature 1011 of the outer tube and the outer stopping lip feature 1001 of the inner tube.

Figure 11:
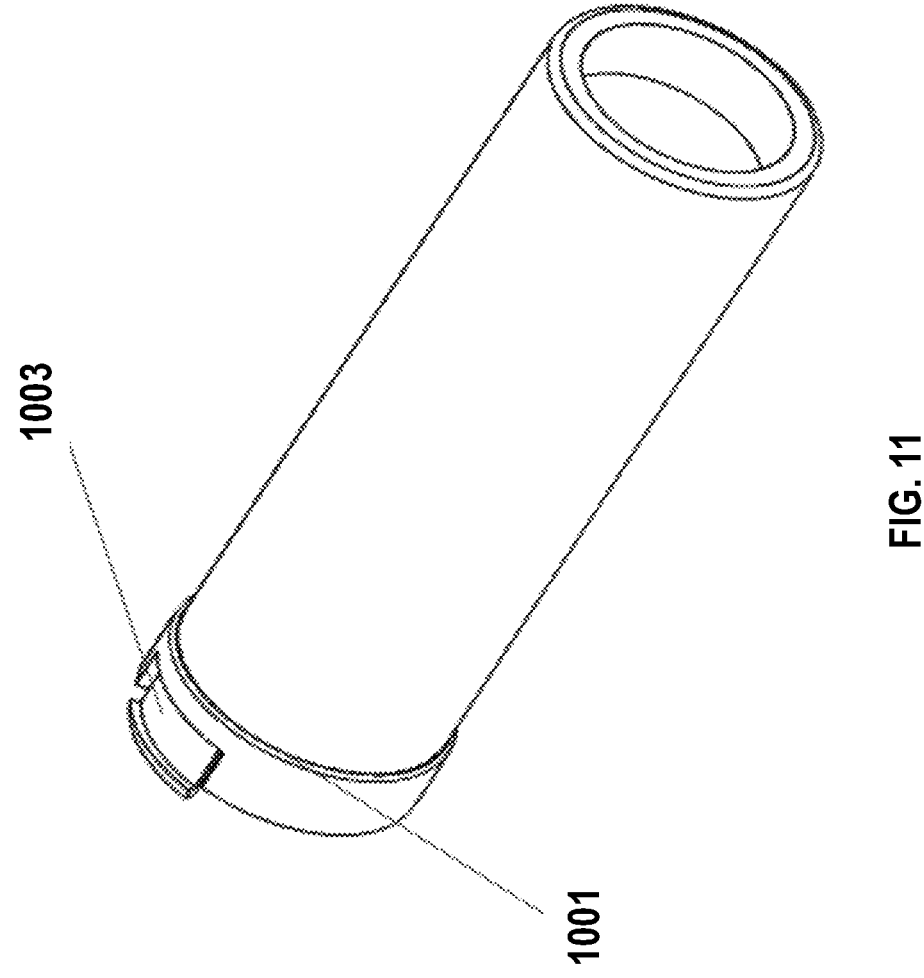
FIG. 11 shows another view of the tube component.

As described above, the tube 1000 may also comprise a snap feature 1003 for engaging with the cap. FIG. 11 shows another view of the tube. The snap feature 1003 may permit the tube to be assembled with cap without any additional coupling means (e.g., adhesives or fasteners).

The tube component can be formed of any suitable material. For example, the tube may be composed of plastic materials to form the snap feature at reduced cost. The suitable material may be non-metallic materials including, but not limited to, polycarbonate, Acrylonitrile Butadiene Styrene, polypropylene, polyurethane (Pebax™), nylon, polyethylene, Delrin™, polyester, Kevlar™, carbon, ceramic, silicone, Kapton™ polyimide, Teflon™ coating, polytetrafluoroethylene (PTFE), plastic (non-porous or porous), latex, polymer, or metallic materials. In some cases, the materials of the modular segments may be selected to reduce friction between the neighboring tubes.

Figure 12A:
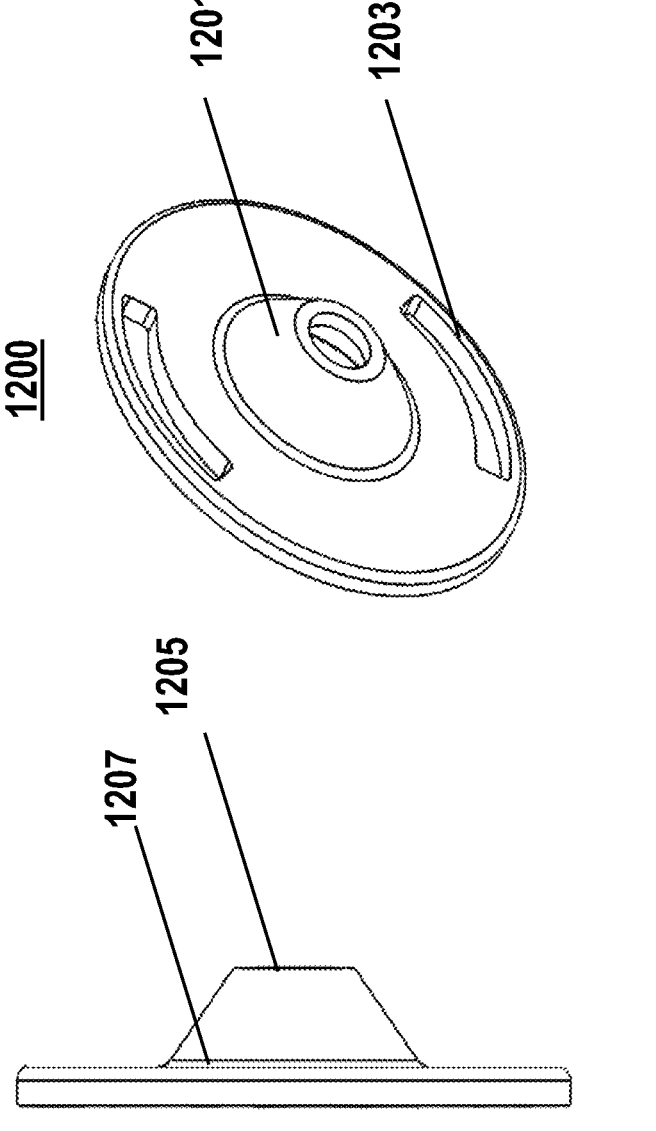
FIG. 12A shows an example of a cap component.
Figure 12B:
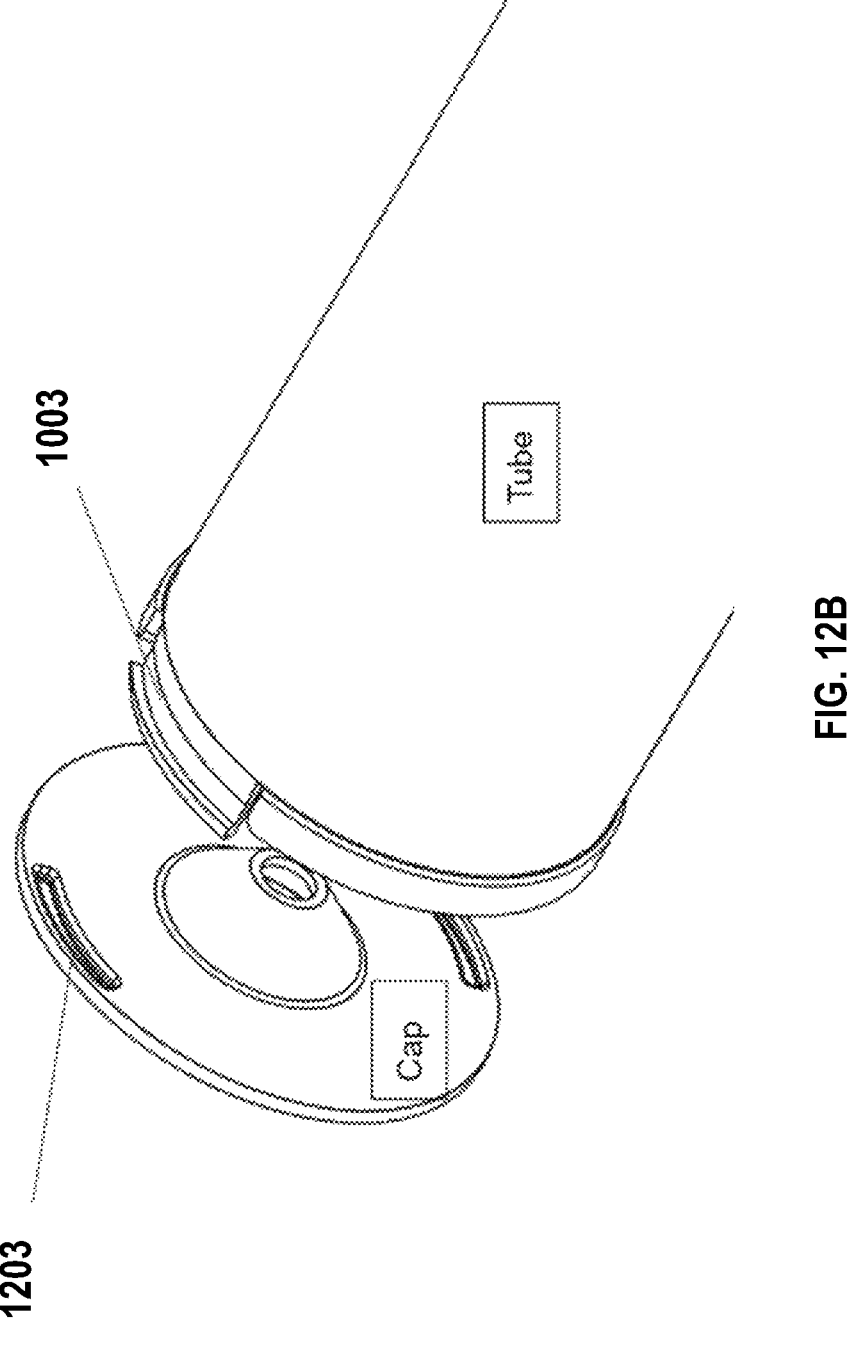
FIG. 12B shows an example of a tube component having a snap feature to engage with the cap component.

FIG. 12A shows an example of a cap component 1200. The cap component includes a support feature to support the catheter during delivery to the patient. The cap component may also act as a stop to prevent the interior modular segments from coming out from the proximal end of the outer modular segment (illustrated in FIG. 13). The cap component 1200 may have an outer dimension/geometrics matching the dimension/geometrics of the outer surface of the tube. The outer dimension/geometrics of the cap component may vary depending on the dimension/geometrics of the corresponding tube. The cap component may comprise a cut out 1203 to engage with the snaps on the tube component for assembly as shown in FIG. 12B. This advantageously allows for easy coupling/releasing a cap from a tube and replacing a cap/tube without additional tools. In some cases, the cap component may be engaged with the respective tube component at the proximal end. Alternatively, the cap component may be engaged with the respective tube component at the distal end.

In some embodiments, the cap component may comprise a support feature 1201 for providing support for the catheter and preventing it from bending/buckling. In some cases, the support feature may have a substantially cone structure. In some cases, the support feature 1201 may have a first opening 1205 (bottom opening of the cone structure) with a diameter slightly larger than catheter/sheath. In some cases, the dimension of the first opening may be selected based on the allowable catheter deflection, catheter diameter, and/or tolerances. For example, the first opening may have greater diameter when greater catheter deflection is allowed.

The diameter of the first opening for the caps of all the modular segments may be the same so that the movement of the catheter may be restricted in the cross-section plane relative to the anti-buckling device in any location along the length. The first opening 1205 located at the center of the caps may allow the catheter to slide smoothly along the driving axis, and when telescope is extended, may provide normal compression to prevent bending or buckling of the catheter. The support feature may have a second opening 1207 (top opening of the cone structure). In some cases, the second opening 1207 may also provide support for the catheter. When the catheter is bent inside the anti-buckling device, it may be in contact with any portion of the support feature or the tube. In some cases, a dimension of the second opening 1207 or the support structure may vary based on the different sizes of the modular segments. The second opening and the support structure may also assist in aligning a plurality of coupled modular segments when they are in a collapse state (illustrated in FIG. 13).

It should be noted that though the support structure is illustrated as a circular cone structure, it can have various shapes (e.g., rectangular cross-section) or dimensions so long as the first opening of the support structure has a dimension/shape corresponding to the dimension/shape of the catheter.

Figure 13:
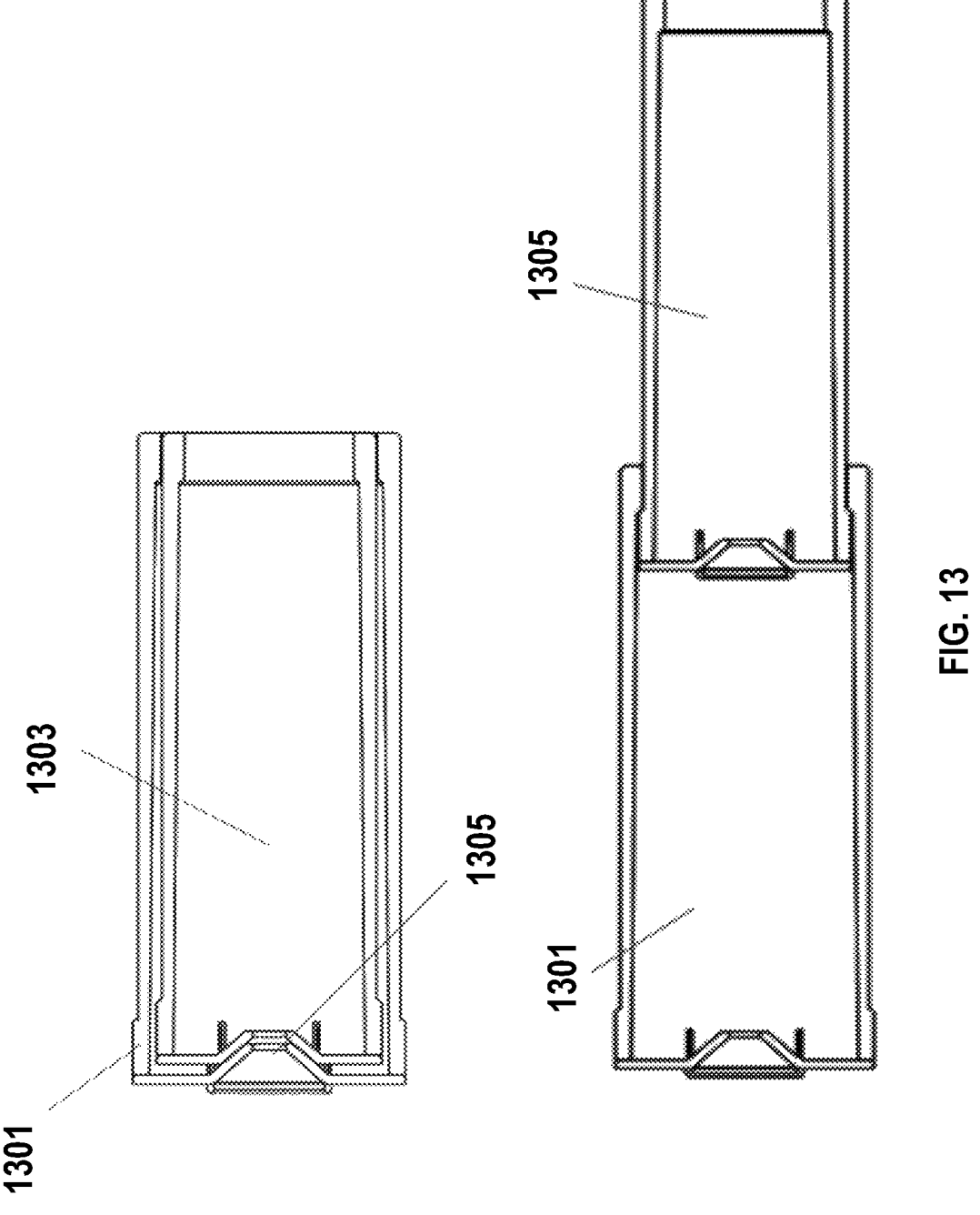
FIG. 13 shows examples of coupled modular segments.

FIG. 13 shows examples of coupled modular segments. The caps of the plurality of the modular segments 1301, 1303 may collectively support the catheter and prevent it from buckling. When the plurality of modular segments/ anti-buckling device collapses, the plurality of caps 1305 may facilitate the plurality of modular segments align with each other. For example, the support structures of the neighboring caps may be stacked and self-centered when the respective modular segments are in the collapse state. When the plurality of modular segments are in the extended state, the inner and outer stopping lip feature of each tube prevents the assembly from separation.

Figure 14:
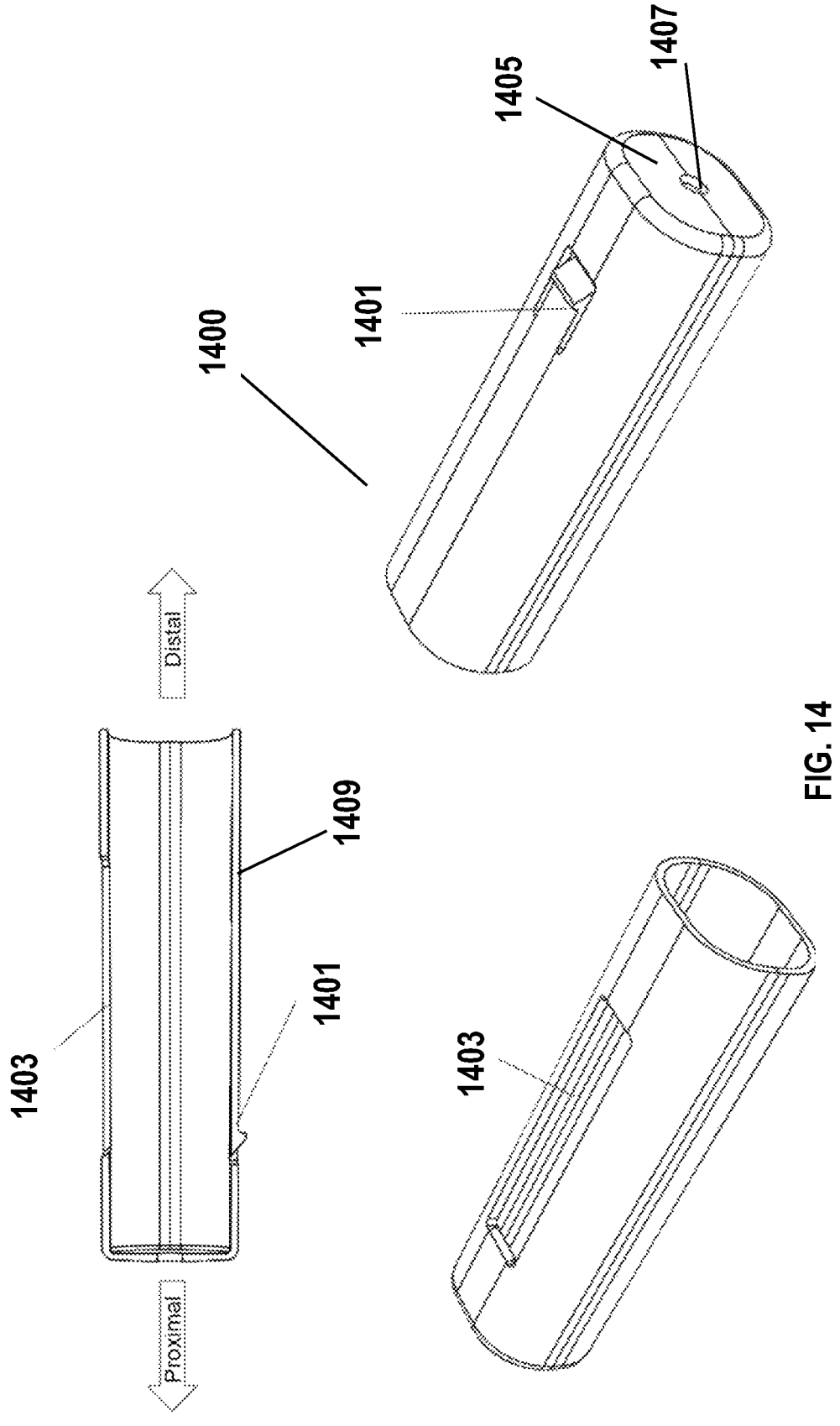
FIGS. 14-16 show another example of a modular segment.
Figure 15:
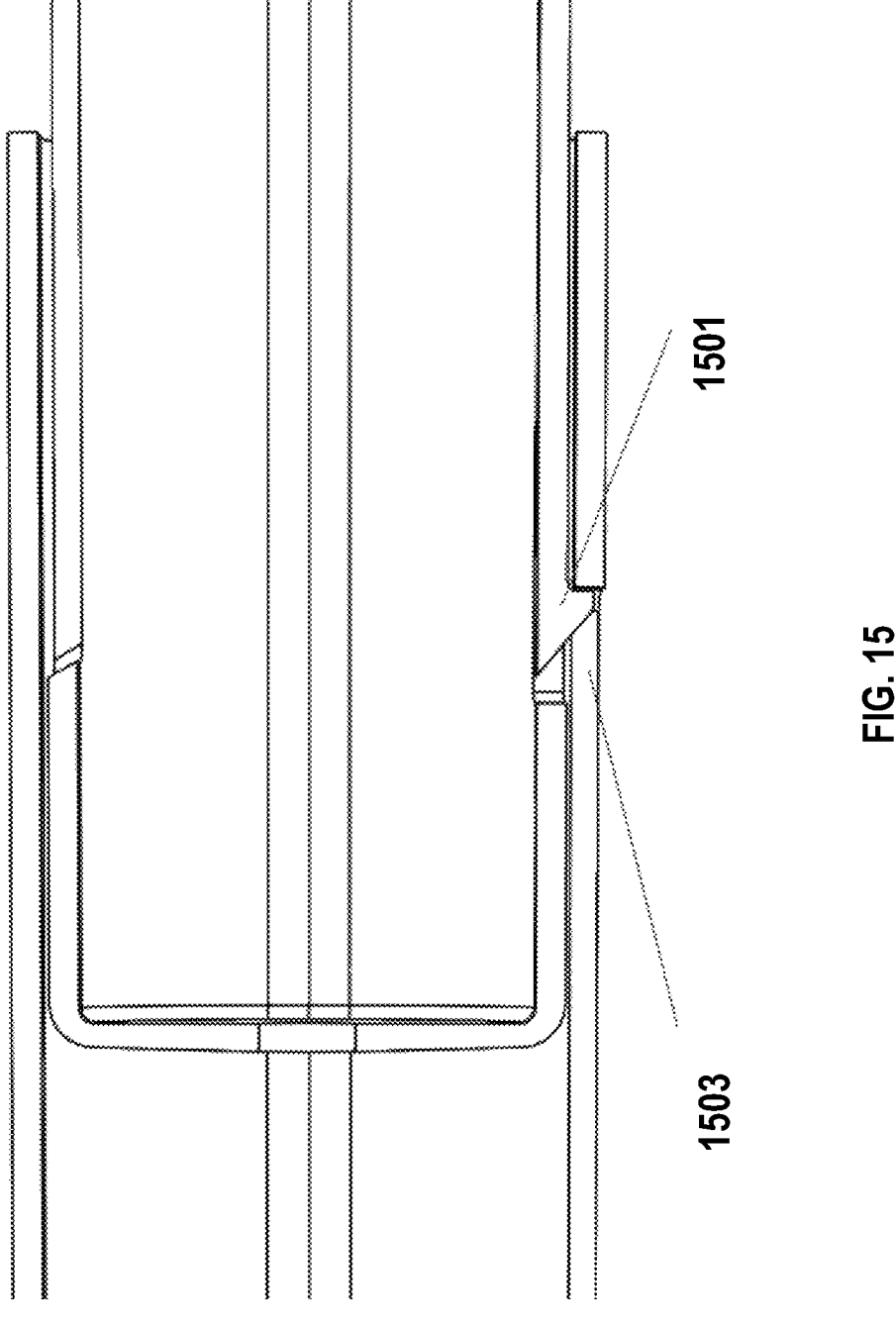
Figure 16:
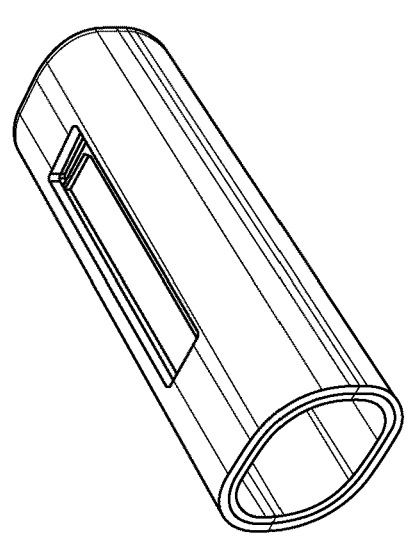
Figure 16:
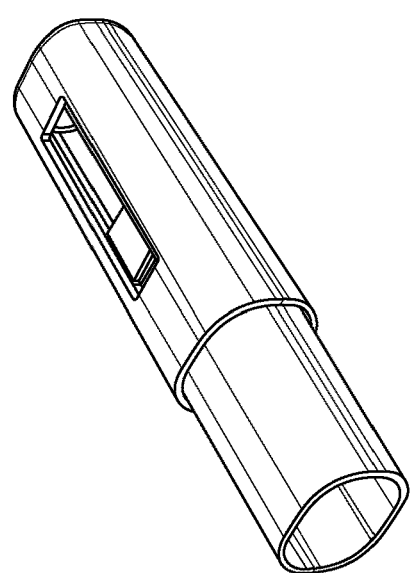
Figure 16:
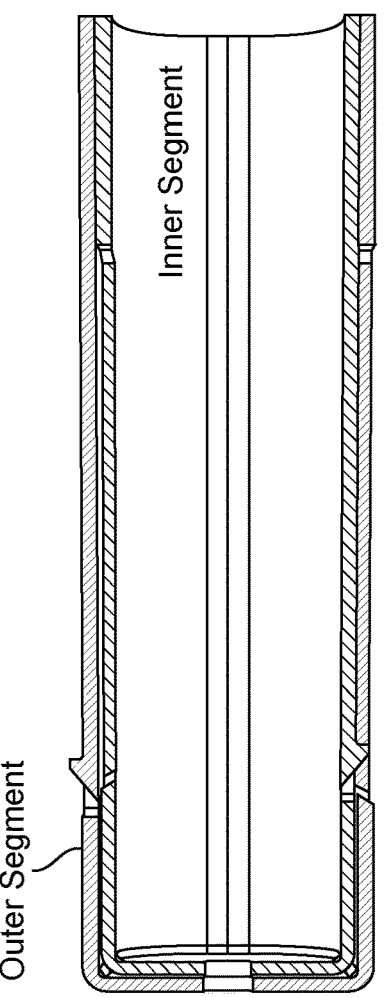
Figure 16:
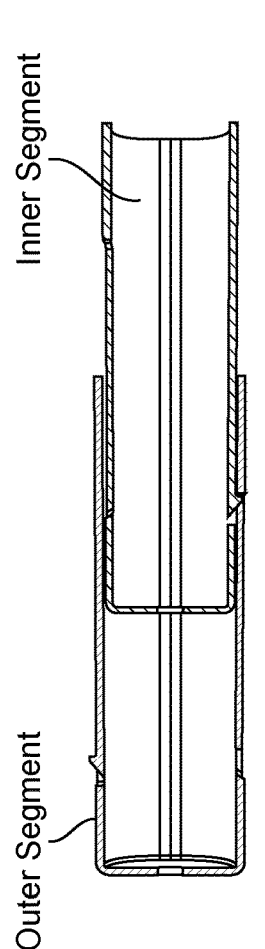

FIGS. 14-16 show another example of a modular segment 1400. The modular segment 1400 may have substantially rectangular cross-section. The modular segment may be a single-piece part. One end of the modular segment may include an end surface 1405 with a clearance hole 1407 to support a catheter. The end surface may be integrally formed with the side wall 1409 of the modular segment. The side wall 1409 may comprise a snap feature 1401 and a cut out window 1403 to allow assembly of multiple modular segments. FIG. 15 illustrates a snap feature of an inner modular segment 1501 engaged with the window 1503 of an outer modular segment. For example, the inner modular segment may be inserted from the proximal end of the outer modular segment and is locked in as the snap feature of the inner modular segment engages with the window of the outer modular segment. This may beneficially allow for assembling modular segments without additional tools or extra coupling means. FIG. 16 shows examples of coupled modular segments in a collapse state and extended state respectively.

Figure 17:
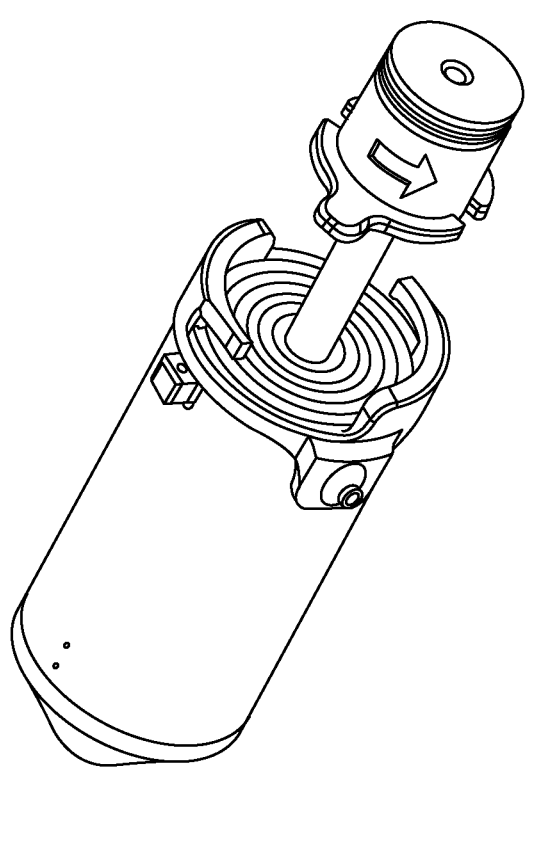
FIGS. 17-18 show examples of an anti-buckling device with a locking feature.
Figure 17:
Figure 17:
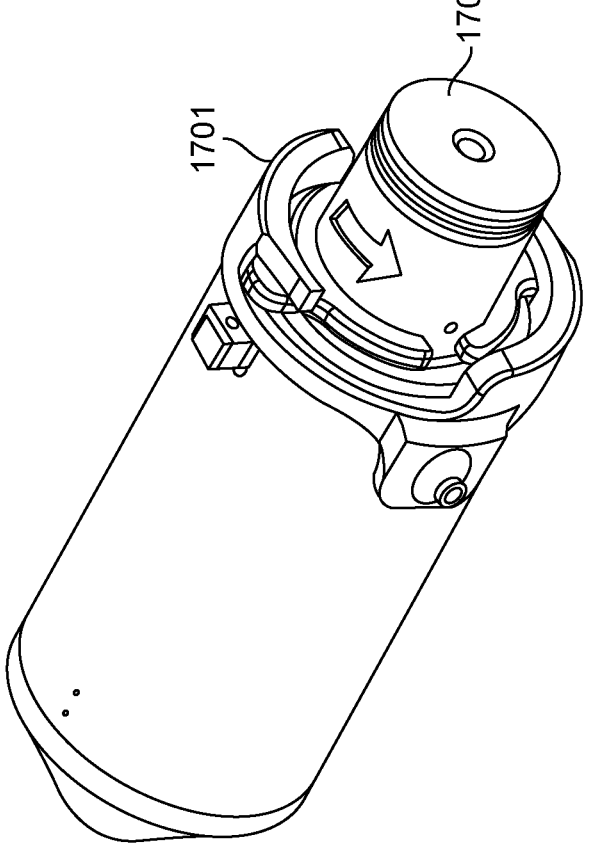
Figure 18:
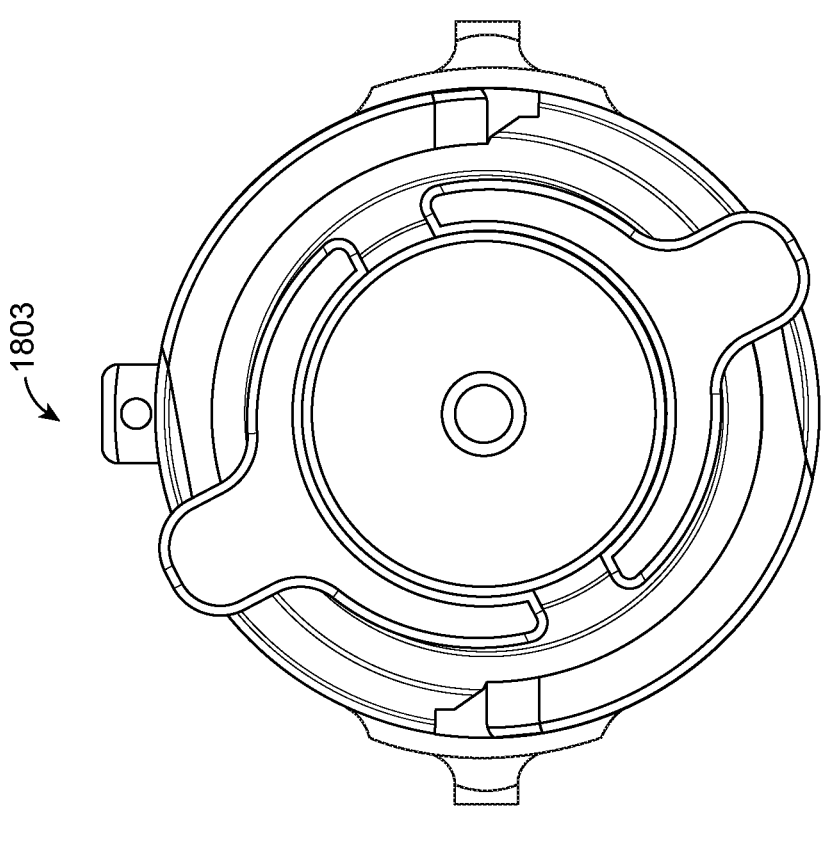
Figure 18:
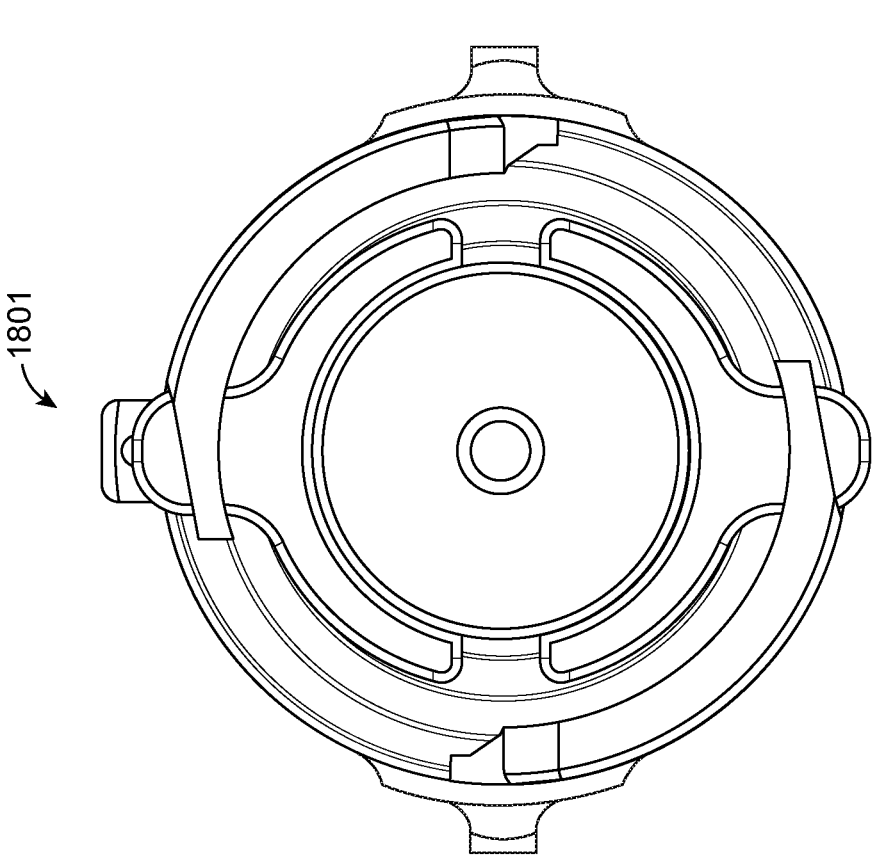
Figure 19:
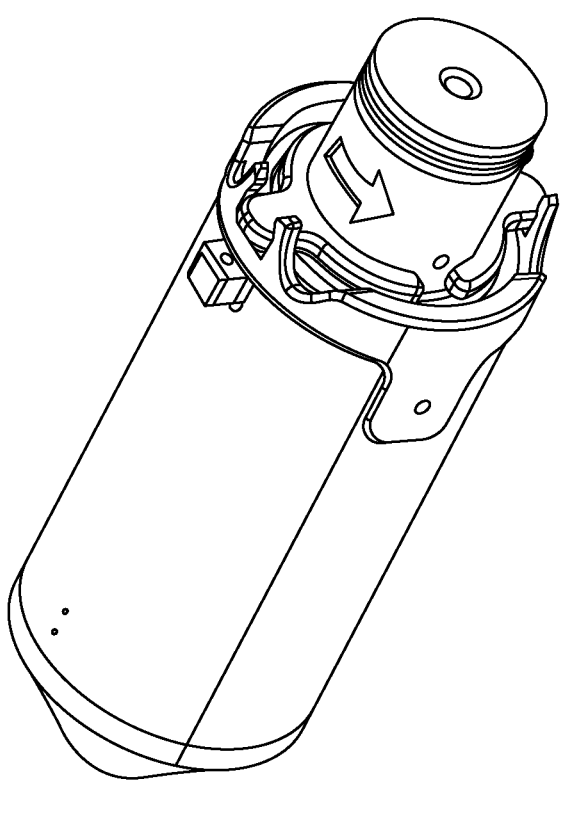
FIG. 19 shows examples of other locking features.
Figure 19:
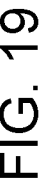
Figure 19:
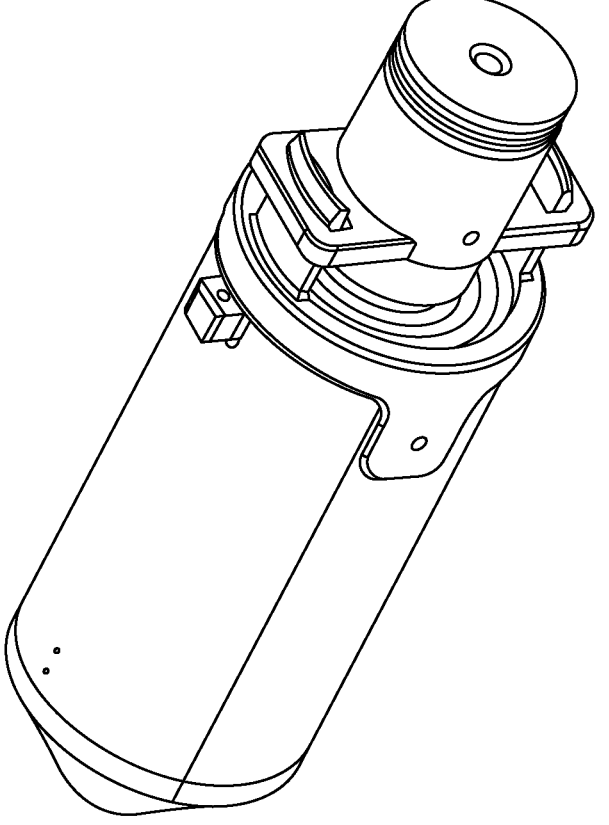

In some embodiments, the anti-buckling device may further comprise a locking feature to prevent the plurality of modular segments from unintentionally extending. The locking feature may prevent the plurality of modular segments from moving (e.g., translational movement along the axis direction) when they are in a collapse state. FIGS. 17-18 show examples of the anti-buckling device with the locking feature. In some embodiments, the innermost (smallest) modular segment may have an extended surface formed with a protruding structure 1703 that engages with a structure formed on the outermost modular segment of the anti-buckling device 1701. The locking feature may be part of a distal end element that is attached to the distal end of the innermost modular segment. When the plurality of modular segments are in a collapsed state, a user may twist the locking feature in one direction to lock the anti-buckling device such as shown in FIG. 18 (e.g., locking state 1801) and unlock the device by rotating in the opposite direction (e.g., unlocking state 1803). FIG. 19 shows examples of other locking features. As shown in the figure, in some cases, a snap feature may be included to create an engagement between the distal end element and the outermost modular segment.

In another aspect, the present disclosure provides an anti-buckling device with a spiral structure. The spiralized anti-buckling device may comprise an extendable and collapsible spiral structure formed of a thin material. The spiralized anti-buckling device may provide unique advantages such as improved, continuum support to the catheter, compact in size, reduced weight/mass of material, and reduced manufacturing cost. FIGS. 20-27 show examples of a spiralized anti-buckling device.

Figure 20:
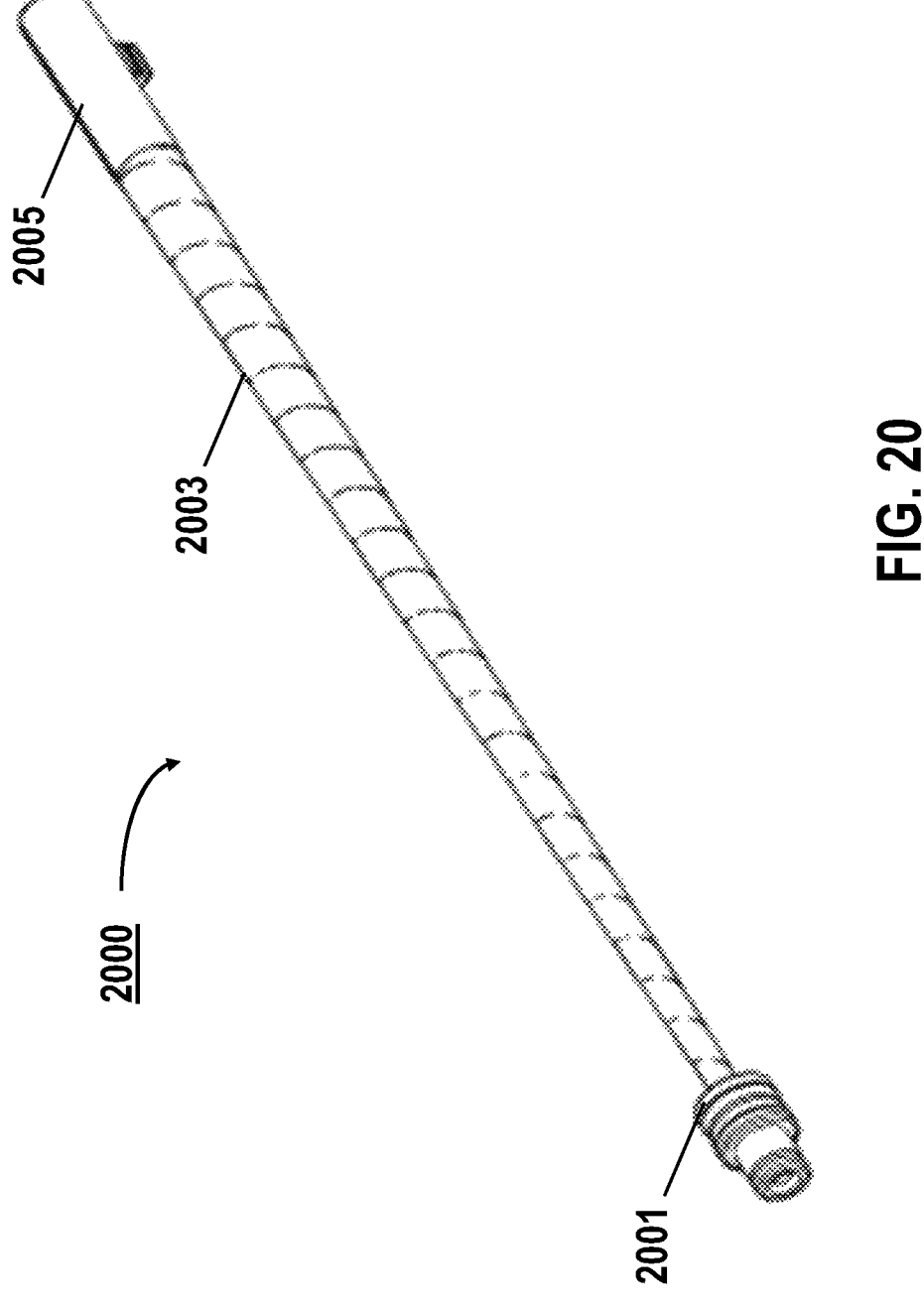
FIG. 20 and FIG. 21 show an example of a spiralized anti-buckling device in an extended state.
Figure 21:
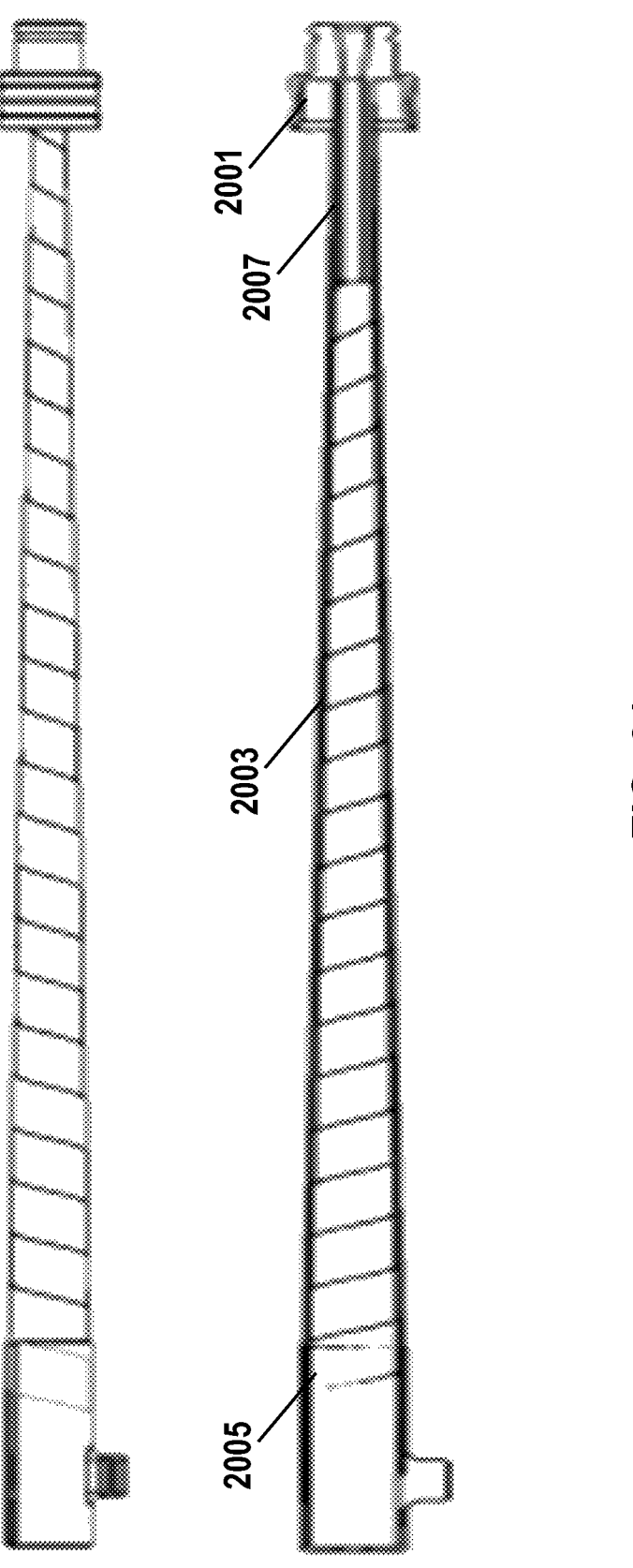
Figure 22:
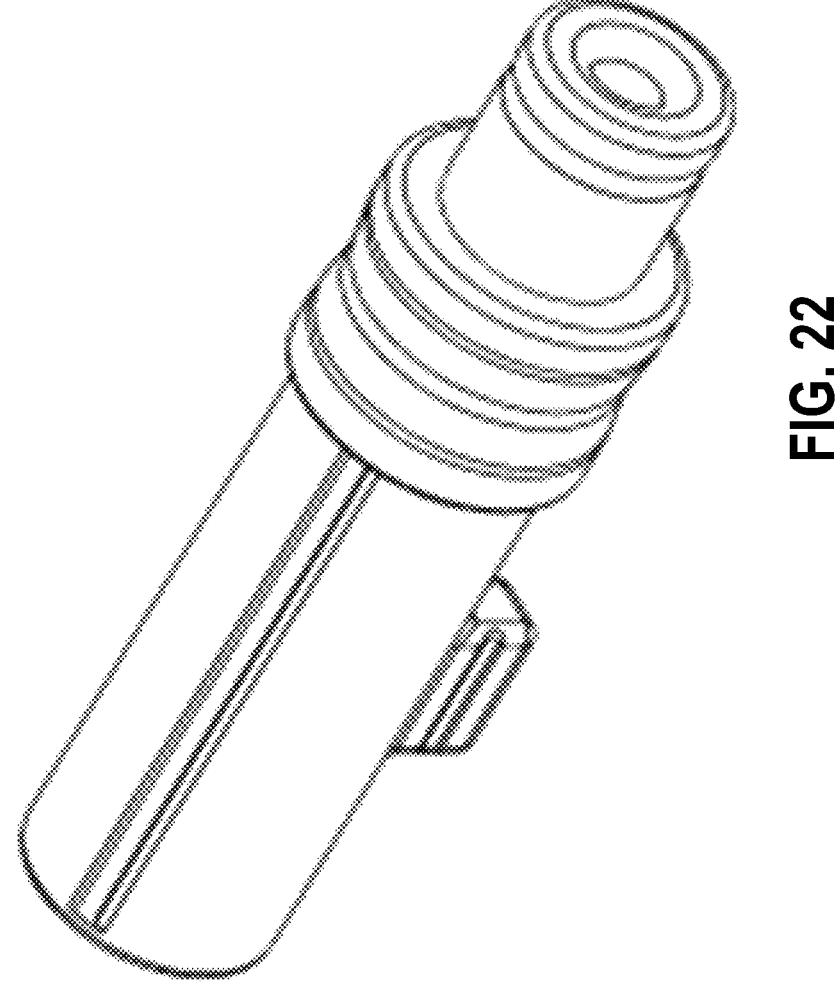
FIG. 22 shows the spiralized anti-buckling device in a collapsed state.

FIG. 20 and FIG. 21 show an example of a spiralized anti-buckling device 2000 in an extended state. FIG. 22 shows the spiralized anti-buckling device in a collapsed state. In some embodiments, the spiralized anti-buckling device 2000 may comprise a plurality of components/structures including a connector component 2001, a spiralized rolling structure 2003, a tube component 2005 and a straw component 2007.

The spiralized rolling structure 2003 may provide support to the catheter. The spiralized rolling structure 2003 may be formed of a thin sheet of material. The thin sheet of material may be capable of being rolled into a desired radius that correspond to a dimension of the catheter. The thin sheet of material may be rolled spirally such that it can be extended and retracted along the longitudinal axis. In some cases, the material may be light weight material such as paper, light-weight and durable material such as polyethylene fibers (e.g., Tyvek), plastic sheets (e.g., polyethylene (PE), poly-propylene (PP)), fabric, sheet metal (e.g., aluminum) and other light and durable materials. The spiralized rolling structure 2003 may be fabricated using any suitable manu-facturing method such as roll forming. This spiralized design along with the thin sheet material may beneficially provide a device with an overall compact size and reduced weight.

The spiralized rolling structure 2003 may have a dimen-sion or size to accommodate the dimension of the catheter. The spiralized rolling structure 2003 may have substantially a cone shape. Unlike the telescoping structure where the catheter is supported by discrete point at each segment, the spiralized rolling structure has a continuously increasing/ decreasing diameter along with length thereby providing continuum support to the catheter.

In some cases, the dimension and the material of the spiralized rolling structure 2003 may be selected to reduce friction between the sheets and/or to optimize for bending and axial stiffness of the device. In some cases, the dimen-sion and the material may be selected such that the device can beneficially prevent excessive buckling at high insertion force. For example, by selecting the proper material and structure that can bear a predetermined amount of force, the rolling structure may noticeably kink and tear when certain amount of force is applied. This advantageously mitigates the possibility of patient injury and provides extra safety as the anti-buckling device breaks before the endoscope system can apply excessive force to the patient. Additionally, since the diameter of the spiralized rolling structure at the proximal end is greater than the outer diameter of the catheter, the catheter may tend to buckle to certain extent. However, due to the continuous supporting to the catheter, such slight buckling may not affect the insertion process. Such buckling is controlled to be within a permissible level by selecting the breaking point (e.g., threshold force) of the spiralized rolling structure as described above.

The tube component 2005 is connected to the spiralized rolling structure 2003 at a proximal end. For example, the outside of the spiralized rolling structure 2003 may attach to the tube component. The tube component 2005 may have features allowing it to be releasably coupled to the robotic endoscope (e.g., the handle portion of the endoscope).

Figure 23:
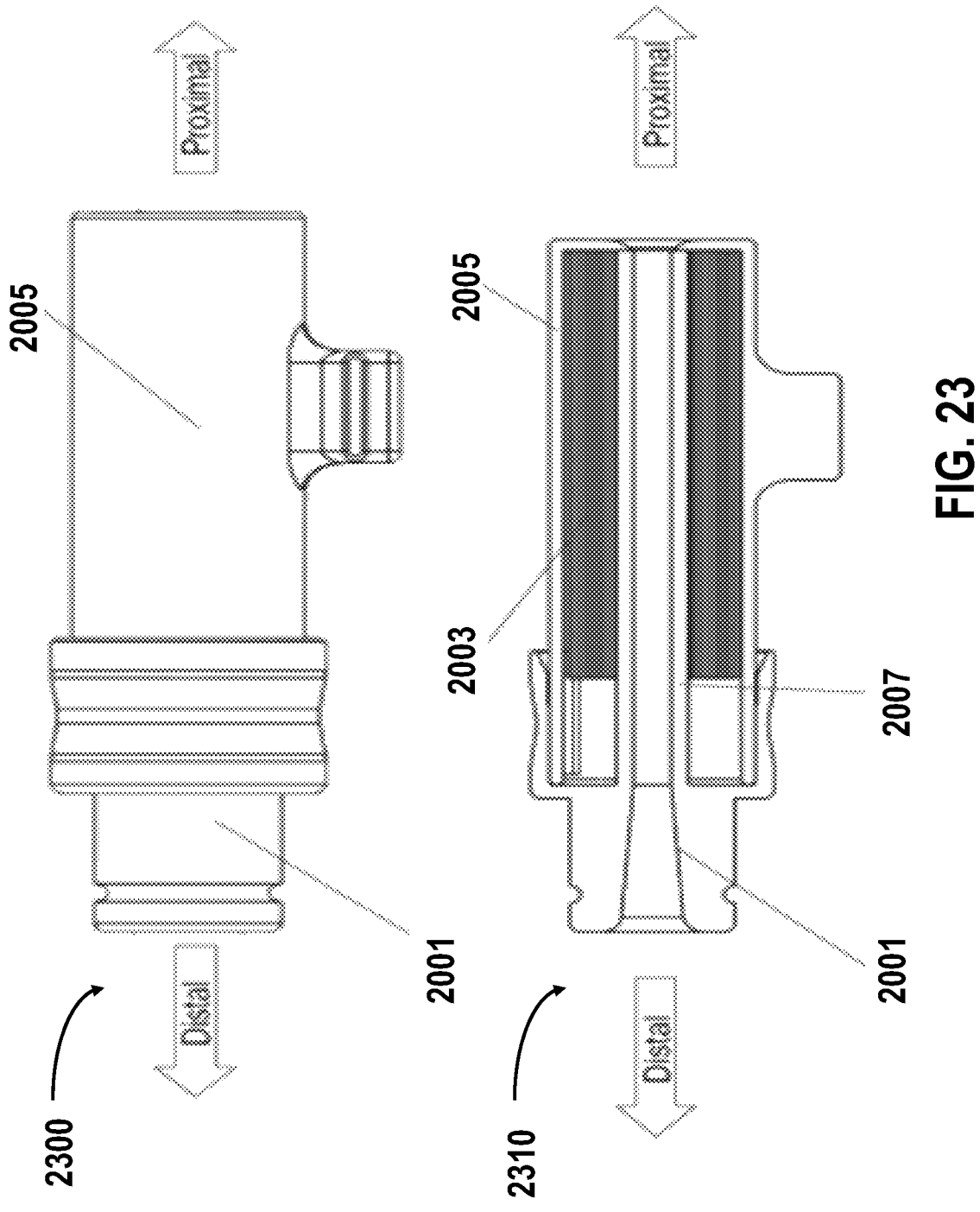
FIG. 23 shows a side view and cross-section view of the spiralized anti-buckling device (in a collapsed state).

The spiralized anti-buckling device may comprise a connector component 2001 at the distal end. The connector component 2001 may be attached to a bedside module during use. FIG. 23 shows a side view 2300 and cross-section view 2310 of the spiralized anti-buckling device (in a collapsed state). The connector component 2001 may act as a "pen cap" for the spiralized anti-buckling device. For example, when the spiralized anti-buckling device is in collapsed state, the connector component 2001 and the tube component 2005 may be connected such as by pushed together so that the connector component may prevent unwanted extension. In some cases, the connector component 2001 and the tube component 2005 may be connected/coupled together via friction fit. Alternatively, other connection features (e.g., locking feature) may be included to releasably connect the connector component 2001 and the tube component 2005. In some cases, the connector component 2001 may have ergonomic features allowing a user to grab when extending the anti-buckling device.

Figure 27:
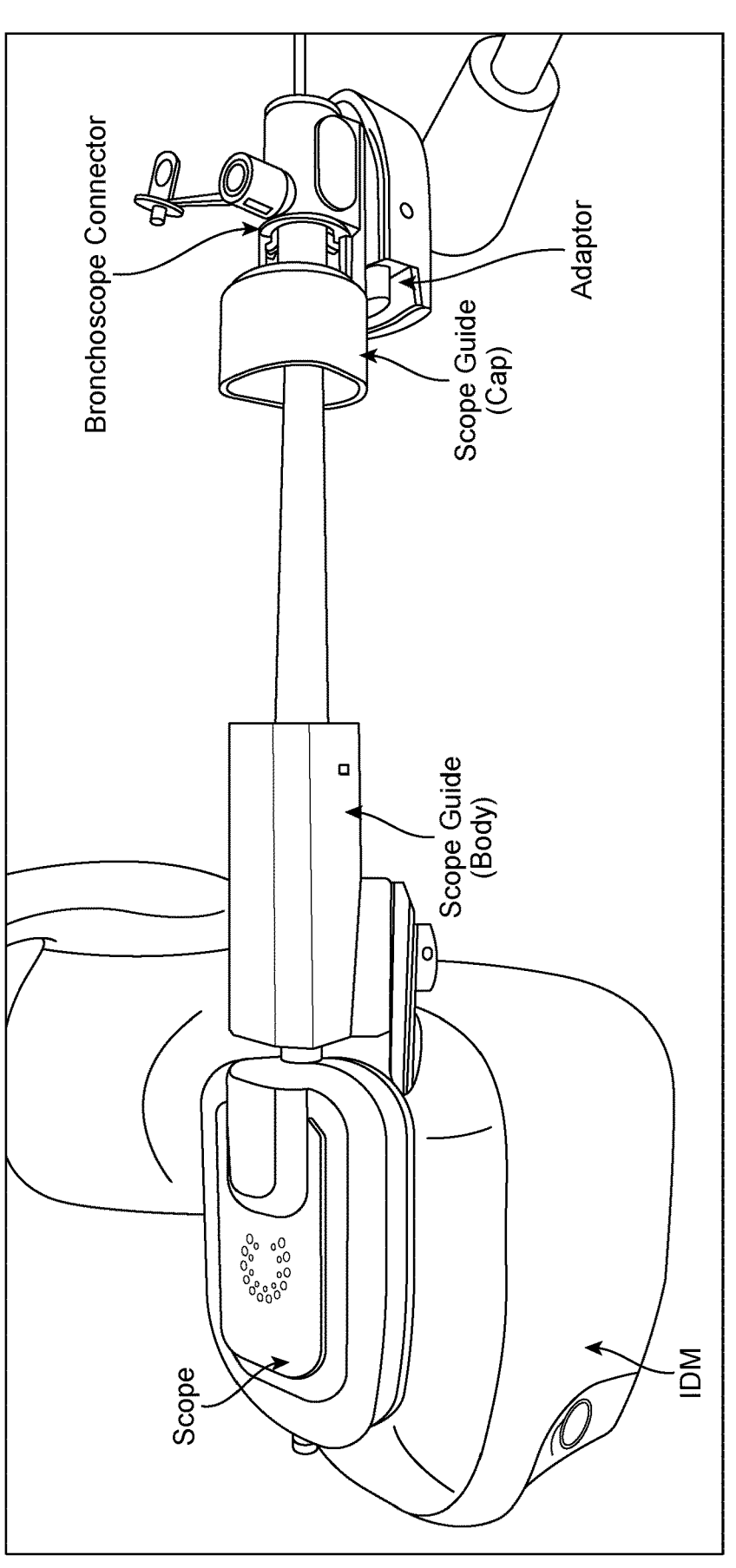
FIG. 27 shows an example of an anti-buckling device with a connector at the distal tip.
Figure 28:
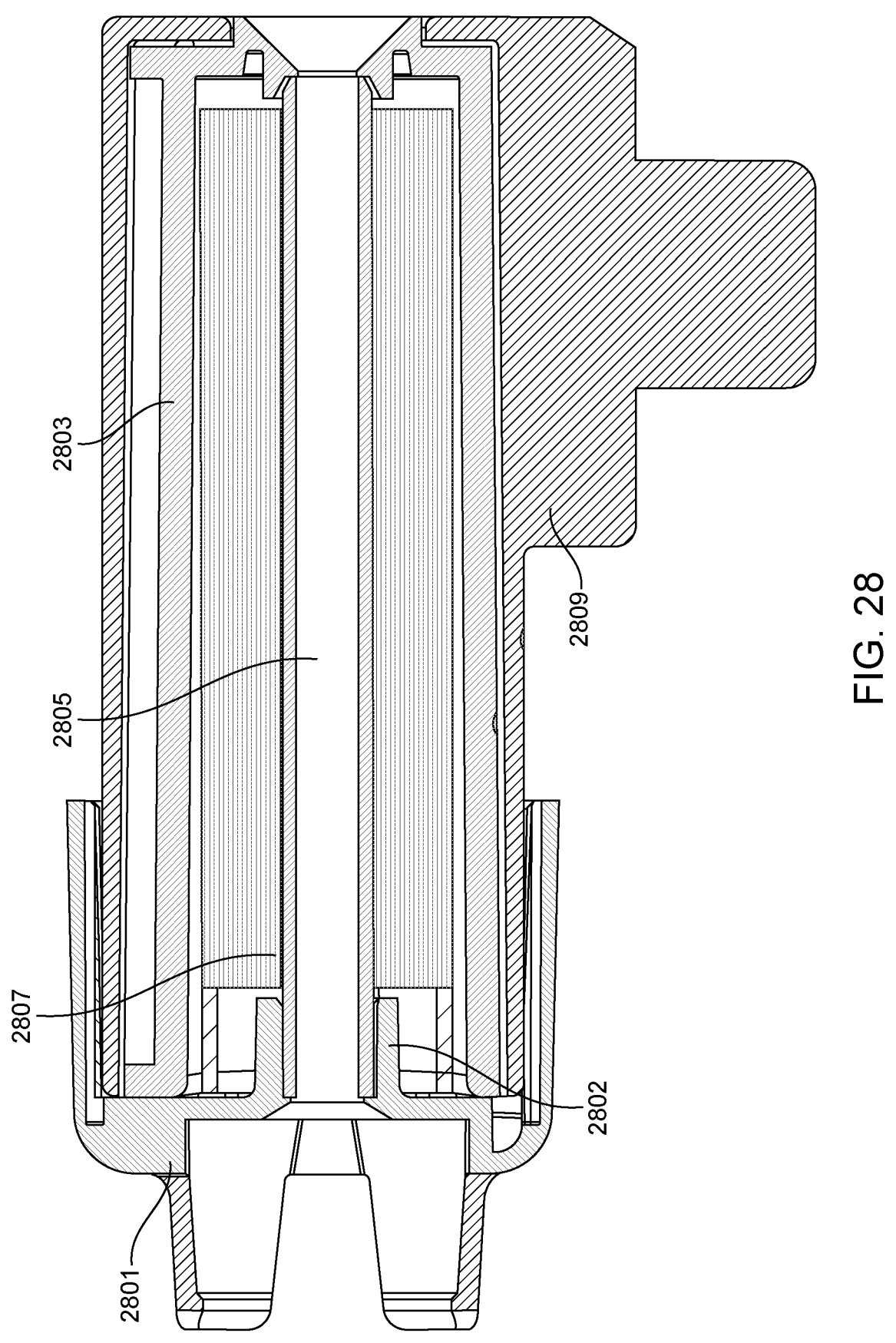
FIG. 28 shows a cross-section view of the anti-buckling device with a connector at the distal tip.

In some embodiments, the connector component 2001 may have substantially a cylindrical shape. The connector component 2001 may have dimensions and geometrics that align it against the outer diameter of the tube component 2005 to provide a friction fit (when in a collapsed state), and center the straw component 2007. The connector may have any other shape or dimension. FIG. 27 shows an example of an anti-buckling device with a different connector design where the shape thereof is not cylindrical. FIG. 28 shows a cross-sectional view of the anti-buckling device in FIG. 27. The connector 2801 may also serve as a cap that can be releasably connected to the tube component 2803 or the proximal main body 2809 in collapsed state. The connector component 2001 may comprise a structure 2802 with dimensions and geometrics that fits the outer diameter of a distal end of the straw component 2805. The distal portion of the straw component 2805 may also be attached to the distal portion of the spiralized rolling structure 2807.

The straw component 2007 may be attached to the connector component 2001 and the distal end of the spiralized rolling structure so as to join the connector component with the spiralized rolling structure. The straw component 2007 may have a substantially cylinder shape with constant diameter. The straw component 2007 may have an outer dimeter matching the smallest dimeter of the spiralized rolling structure. In some cases, the straw component 2007 may be integrally formed with the connector component. For instance, the straw component and the connector component may be formed as a single piece using injection molding or other suitable method. Alternatively, the straw component 2007 may be formed as a separate part and assembled to the connector component and rolling structure. For example, the straw component may be manufactured by extrusion and assembled to the connector component.

In some cases, the straw component 2007 may comprise a self-centering feature to assist in alignment. The self-centering feature may guidance alignment of the anti-buckling device when it is collapsed. For example, the proximal end of the straw component 2007 may have a funnel-shaped feature (e.g., male part), and when the anti-buckling device is closed the male funnel-shaped feature may self-center by interfacing with a cone shape of the rolling structure or the tube component with a larger diameter (e.g., female part).

Figure 24:
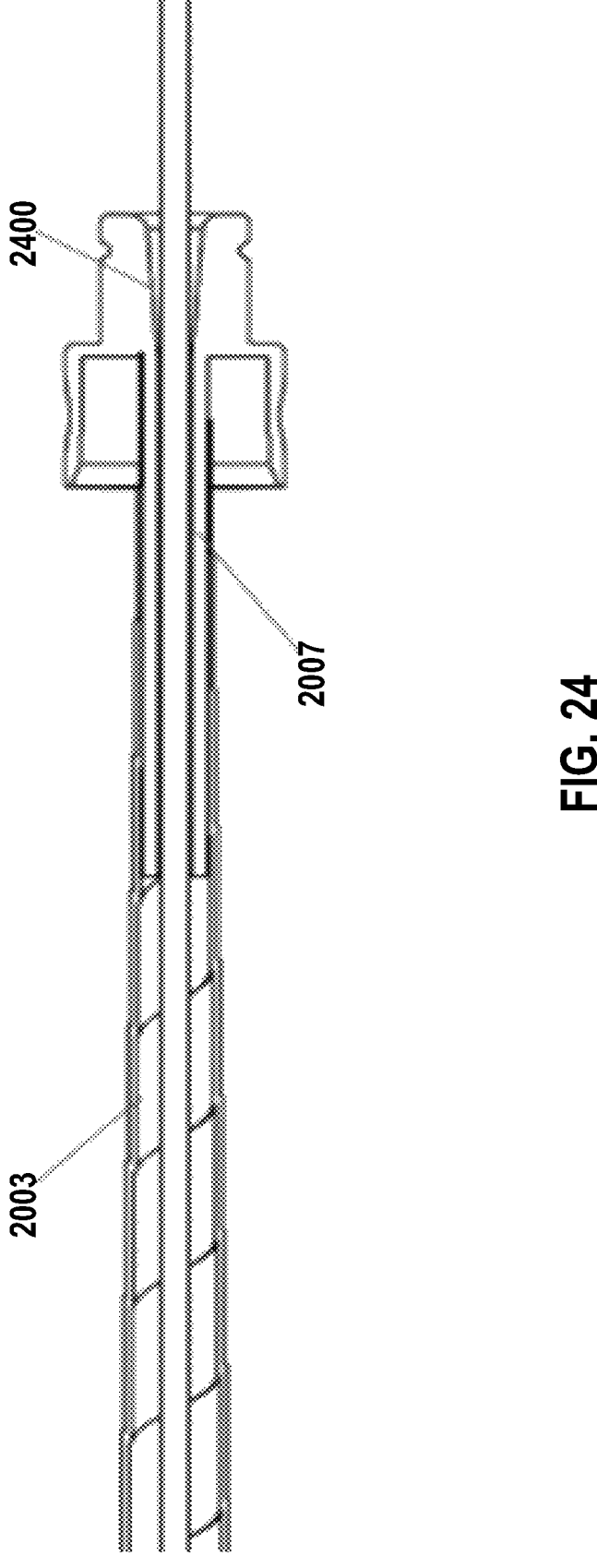
FIG. 24 shows an example of a catheter inserted into the anti-buckling device.

The straw component may be in contact with the distal end of the catheter thereby providing support to the distal end of the catheter. FIG. 24 shows an example of a catheter 2400 inserted into the anti-buckling device. The distal end of the catheter 2300 is supported by the straw component 2007. The dimension of the straw component (e.g., diameter) may be dependent on the dimeter of the catheter. In some cases, the length of the straw component may be selected to provide sufficient friction with the rolling structure. The dimension of the rolling structure such as the diameter at the distal end may be dependent on the dimeter of the straw component while the diameter at the proximal end may correspond to the diameter of the tube component.

The tube component 2005 is connected to the spiralized rolling structure 2003 at the proximal end. For example, the outside of the spiralized rolling structure 2003 may attach to the tube component. The tube component 2005 may have features allowing it to be releasably coupled to the robotic endoscope (e.g., the handle portion of the endoscope).

Figure 25:
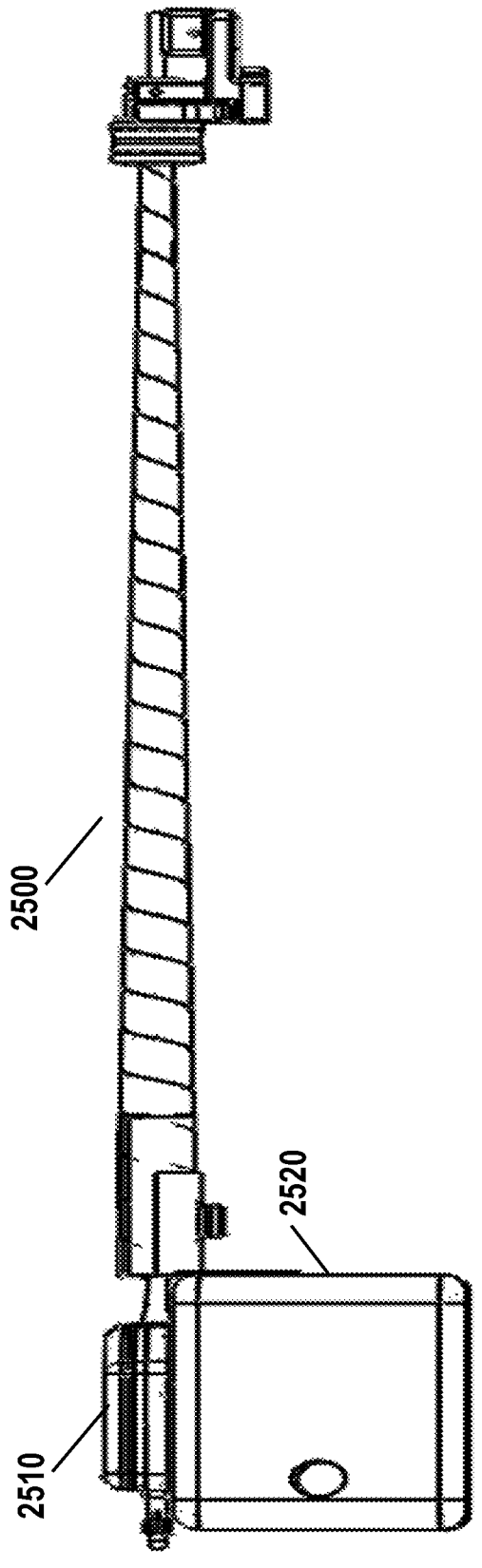
FIG. 25 and FIG. 26 show examples of an assembly of the anti-buckling device and the catheter assembly.
Figure 26:
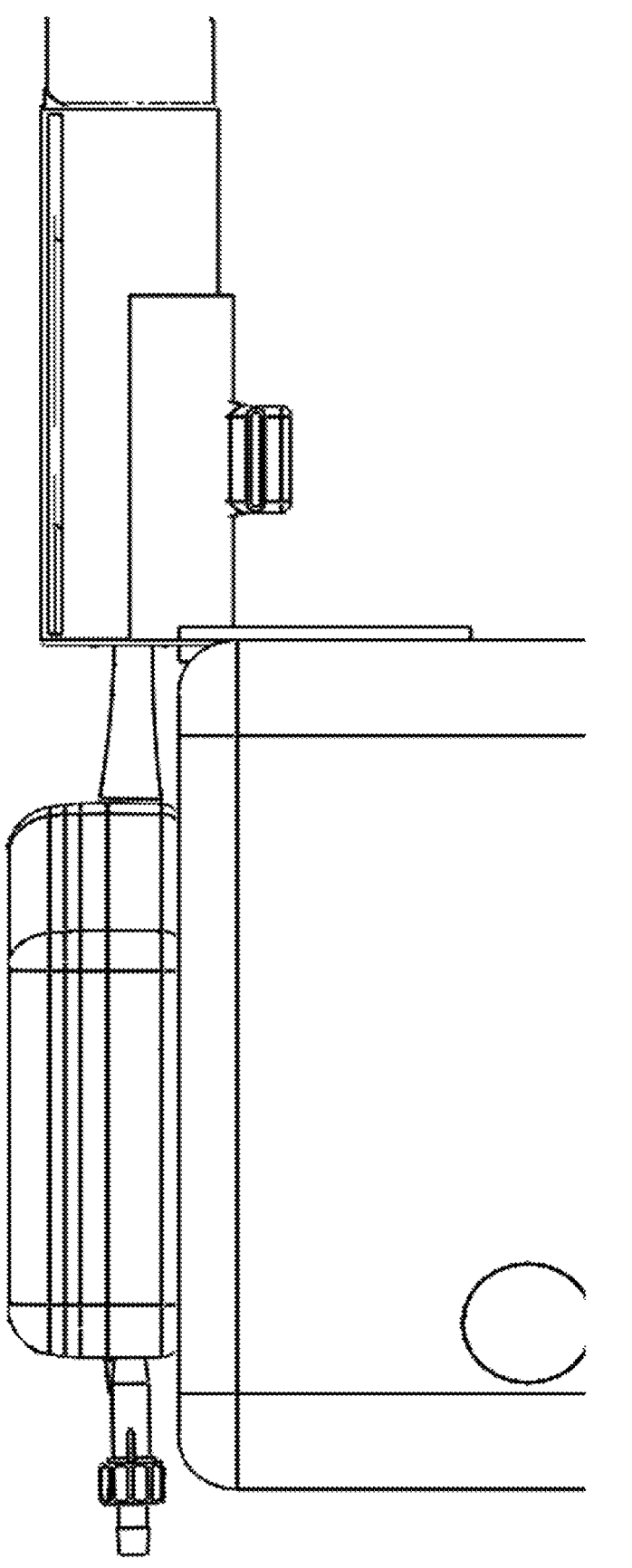

As described above, the system and devices herein may allow for a simplified set-up flow for assembling the anti-buckling mechanism and the endoscope. For example, the anti-buckling mechanism and scope handle may be assembled via a removable connection between the anti-buckling mechanism and the scope handle and top-load the assembled pieces as a single piece onto the instrument driving mechanism. This convenient assembly capability beneficially allows coupling the scope handle and anti-buckling assembly to the robotic arm regardless the state and current position of the instrument driving mechanism. FIG. 25 and FIG. 26 show examples of the assembly of the anti-buckling device 2500 and the catheter assembly 2510. In some cases, the spiralized anti-buckling device may be a separable device that can be disposed of after single use. The spiralized anti-buckling device can be releasably connected to the handle of the catheter assembly 2510 via a connection feature. This allows a user to place the connected assembly of anti-buckling device and scope onto the instrument driving mechanism 2520 (e.g., robotic capital equipment) via the interface of the handle.

As described above, the provided spiralized anti-buckling device may allow for a light and compact design with reduced cost. The spiralized rolling structure may be formed of a thin sheet of material that can be light and durable. These tube component, connector component and straw component may be comprised of plastic materials, thermoplastic polymer such as Acrylonitrile Butadiene Styrene, polypropylene, polyurethane (Pebax™) nylon, polyethylene, Delrin™, polyester, PE, PP and various others. In some cases, other non-plastic materials such as metal can be utilized. These components can be manufactured easily (e.g., injection molding) with reduced cost. injection molded plastic. Any suitable manufacturing method such as 3D printing (e.g., powder based processes such as multi jet fusion, plaster-based 3D printing (PP)), CNC machining and blow molding can also be adopted.

Although embodiments of the anti-buckling device have been described with reference to a medical robotic system, it should be noted that the anti-buckling device described herein may be used to provide anti-buckling feature for any medical device having an elongate and flexible configuration. For example, in other embodiments, embodiments of the anti-buckling device described herein may be used to support any flexible tool in the field of medicine, such as an endoscope, a flexible grasper, laser fibers, etc.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. An anti-buckling device comprising:
a spiralized rolling structure configured for supporting a catheter of an endoscopic device, wherein the spiralized rolling structure is formed of a sheet of material rolled spirally such that at least a portion of the sheet of material overlaps with another portion of the sheet of the material, and wherein the spiralized rolling structure is extendable or retractable along a longitudinal axis of the spiralized rolling structure;
a first component connected to a distal end of the spiralized rolling structure; and
a second component is connected to a proximal end of the spiralized rolling structure,
wherein the first component is configured to connect releasably with the second component.

2. The anti-buckling device of claim 1, wherein the material is paper or fabric.

3. The anti-buckling device of claim 1, wherein the first component is configured to releasably couple the anti-buckling device to a component at a patient bed.

4. The anti-buckling device of claim 1, wherein the second component is configured to releasably couple the anti-buckling device to a handle portion of the elongate member.

5. The anti-buckling device of claim 1, wherein the spiralized rolling structure is configured to provide a continuous support to the elongate member.

6. The anti-buckling device of claim 1, wherein the first component is configured to connect to the distal end of the spiralized rolling structure via a third component.

7. The anti-buckling device of claim 6, wherein the third component is configured to support a distal end of the elongate member.

8. The anti-buckling device of claim 6, wherein the third component comprises a self-centering feature to assist in alignment when the anti-buckling device is in the collapsed state.

* * * * *